United States Patent
Brown

(10) Patent No.: US 10,262,102 B2
(45) Date of Patent: Apr. 16, 2019

(54) SYSTEMS AND METHODS FOR GENOTYPING WITH GRAPH REFERENCE

(71) Applicant: Seven Bridges Genomics Inc., Cambridge, MA (US)

(72) Inventor: Richard Brown, London (GB)

(73) Assignee: Seven Bridges Genomics Inc., Charlestown, MA (US)

( * ) Notice: Subject to any disclaimer, the term of this patent is extended or adjusted under 35 U.S.C. 154(b) by 350 days.

(21) Appl. No.: 15/052,354

(22) Filed: Feb. 24, 2016

(65) Prior Publication Data

US 2017/0242958 A1    Aug. 24, 2017

(51) Int. Cl.
| G01N 33/48 | (2006.01) |
| G01N 33/50 | (2006.01) |
| G06F 19/18 | (2011.01) |
| G06F 19/26 | (2011.01) |

(52) U.S. Cl.
CPC ............. *G06F 19/18* (2013.01); *G06F 19/26* (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,511,158 A | 4/1996 | Sims |
| 5,583,024 A | 12/1996 | McElroy et al. |
| 5,674,713 A | 10/1997 | McElroy et al. |
| 5,700,673 A | 12/1997 | McElroy et al. |
| 5,701,256 A | 12/1997 | Marr et al. |
| 6,054,278 A | 4/2000 | Dodge et al. |
| 6,210,891 B1 | 4/2001 | Nyren et al. |
| 6,223,128 B1 | 4/2001 | Allex et al. |
| 6,306,597 B1 | 10/2001 | Macevicz |
| 6,582,938 B1 | 6/2003 | Su et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,577,554 B2 | 8/2009 | Lystad et al. |
| 7,580,918 B2 | 8/2009 | Chang et al. |
| 7,598,035 B2 | 10/2009 | Macevicz |
| 7,620,800 B2 | 11/2009 | Huppenthal et al. |
| 7,776,616 B2 | 8/2010 | Heath et al. |
| 7,809,509 B2 | 10/2010 | Milosavljevic |
| 7,835,871 B2 | 11/2010 | Kain et al. |
| 7,885,840 B2 | 2/2011 | Sadiq et al. |
| 7,917,302 B2 | 3/2011 | Rognes |
| 7,957,913 B2 | 6/2011 | Chinitz et al. |
| 7,960,120 B2 | 6/2011 | Rigatti et al. |
| 8,146,099 B2 | 3/2012 | Tkatch et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,639,847 B2 | 1/2014 | Blaszczak et al. |
| 9,063,914 B2 | 6/2015 | Kural et al. |
| 9,092,402 B2 | 7/2015 | Kural et al. |
| 9,116,866 B2 | 8/2015 | Kural |
| 9,390,226 B2 | 7/2016 | Kural |
| 9,817,944 B2 | 11/2017 | Kural |
| 2002/0164629 A1 | 11/2002 | Quake et al. |
| 2002/0190663 A1 | 12/2002 | Rasmussen |
| 2004/0023209 A1 | 2/2004 | Jonasson |

(Continued)

FOREIGN PATENT DOCUMENTS

| KR | 101282798 B1 | 7/2013 |
| WO | 2007/086935 A2 | 8/2007 |

(Continued)

OTHER PUBLICATIONS

Craig et al. Ordering of cosmid clones covering the Herpes simplex virus type I (HSV-I) genome: a test case for fingerprinting by hybiridsation. Nucleic Acids Research, vol. 18, pp. 2653-2660. (Year: 1990).*
Golub et al. Molecular classification of cancer: class discovery and class prediction by gene expression monitoring. Science, pp. 531-537. (Year: 1999).*
Rajaram, 2013, Pearl millet [*Pennisetum glaucum* (L.) R. Br.] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.

(Continued)

*Primary Examiner* — Russell S Negin
(74) *Attorney, Agent, or Firm* — Kip L. Bodi

(57) ABSTRACT

Genomic references are structured as a reference graph that represents diploid genotypes in organisms. A path through a series of connected nodes and edges represents a genetic sequence. Genetic variation within a diploid organism is represented by multiple paths through the reference graph. The graph may be transformed into a traversal graph in which a path represents a diploid genotype. Genetic analysis using the traversal graph allows an organism's diploid genotype to be elucidated, e.g., by mapping sequence reads to the reference graph and scoring paths in the traversal graph based on the mapping to determine the path through the traversal graph that best fits the sequence reads.

20 Claims, 14 Drawing Sheets

(56) References Cited

U.S. PATENT DOCUMENTS

| | | |
|---|---|---|
| 2005/0089906 A1 | 4/2005 | Furuta et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0114362 A1 | 5/2007 | Feng et al. |
| 2007/0166707 A1 | 7/2007 | Schadt et al. |
| 2008/0003571 A1 | 1/2008 | McKeman et al. |
| 2008/0077607 A1 | 3/2008 | Gatawood et al. |
| 2008/0251711 A1 | 10/2008 | Reilly |
| 2008/0281463 A1 | 11/2008 | Suh et al. |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1 | 6/2009 | Brodzik et al. |
| 2009/0191565 A1 | 7/2009 | Lapidus et al. |
| 2009/0233809 A1 | 9/2009 | Faham et al. |
| 2009/0300781 A1 | 12/2009 | Bancroft et al. |
| 2009/0318310 A1 | 12/2009 | Liu et al. |
| 2009/0325145 A1 | 12/2009 | Sablon et al. |
| 2010/0010992 A1 | 1/2010 | Morris |
| 2010/0035252 A1 | 2/2010 | Rothberg et al. |
| 2010/0041048 A1 | 2/2010 | Diehl et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0285578 A1 | 11/2010 | Selden et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2011/0257889 A1 | 10/2011 | Klammer et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0045771 A1 | 2/2012 | Beier et al. |
| 2012/0157322 A1 | 6/2012 | Myllykangas et al. |
| 2012/0239706 A1 | 9/2012 | Steinfadt |
| 2012/0330566 A1 | 12/2012 | Chaisson |
| 2013/0029879 A1 | 1/2013 | Shetty et al. |
| 2013/0035904 A1 | 2/2013 | Kuhn |
| 2013/0059738 A1* | 3/2013 | Leamon ............... C12Q 1/6855 506/2 |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0232480 A1 | 9/2013 | Winterfeldt et al. |
| 2013/0289099 A1* | 10/2013 | Le Goff ............. C12N 15/1138 514/44 A |
| 2013/0311106 A1 | 11/2013 | White et al. |
| 2013/0345066 A1 | 12/2013 | Brinza et al. |
| 2014/0012866 A1 | 1/2014 | Bowman et al. |
| 2014/0025312 A1 | 1/2014 | Chin et al. |
| 2014/0051588 A9 | 2/2014 | Drmanac et al. |
| 2014/0066317 A1* | 3/2014 | Talasaz ............... C12Q 1/6869 506/2 |
| 2014/0129201 A1 | 5/2014 | Kennedy et al. |
| 2014/0136120 A1 | 5/2014 | Colwell et al. |
| 2014/0200147 A1 | 7/2014 | Bertha et al. |
| 2014/0278590 A1 | 9/2014 | Abbassi et al. |
| 2014/0280360 A1 | 9/2014 | Webber et al. |
| 2014/0281708 A1 | 9/2014 | Adam et al. |
| 2014/0323320 A1 | 10/2014 | Jia et al. |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0094212 A1 | 4/2015 | Gottimukkala et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Grose et al. |
| 2017/0242958 A1 | 8/2017 | Brown |

FOREIGN PATENT DOCUMENTS

| | | |
|---|---|---|
| WO | 2010/010992 A1 | 1/2010 |
| WO | 2012/096579 A2 | 7/2012 |
| WO | 2012/098515 A1 | 7/2012 |
| WO | 2012/142531 A2 | 10/2012 |
| WO | 2013/035904 A1 | 3/2013 |
| WO | 2013043909 A1 | 3/2013 |
| WO | 2013/106737 A1 | 7/2013 |
| WO | 2013184643 A1 | 12/2013 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 20161412948 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Rognes, 2000, Six-fold speed-up of Smith-Waterman sequence database searching using parallel processing on common microprocessors, Bioinformatics 16(8):699-706.

Rognes, 2001, ParAlign: a parallel sequence alignment algorithm for rapid and sensitive database searches, Nucl Ac Res 29(7):1647-1652.

Rognes, 2011, Faster Smith-Waterman database searches with inter-sequence SIMD parallelisation, Bioinformatics 12:221.

Ronquist, 2012, MrBayes 12: efficient Bayesian phylogenetic inference and model choice across a large model space, Syst Biol 61(3):539-42.

Rothberg, 2011, An integrated semiconductor device enabling non-optical genome sequencing, Nature 475:348-352.

Saebo, 2005, PARALIGN: rapid and sensitive sequence similarity searches powered by parallel computing technology, Nucl Ac Res 33:W535-W539.

Sato, 2008, Directed acyclic graph kernels for structural RNA analysis, BMC (BioMed Central) Bioinformatics 9(318).

Schenk 2013, A pipeline for comprehensive and automated processing of electron diffraction data in IPLT, J Struct Biol 182(2):173-185.

Schneeberger, 2009, Sumaltaneous alignment of short reads against multiple genomes, Genome Biol 10(9):R98.2-R98.12.

(56) References Cited

OTHER PUBLICATIONS

Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5) 596-609.
Soni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing_pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tan, 2010, A Comparison of Using Taverna and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Tarhio, 1993, Approximate Boyer-Moore String Matching, SIAM J Comput 22(2):243-260.
The 1000 Genomes Project, 2015, A global reference for human genetic variation, Nature 526:68-74.
Thomas, 2014, Community-wide effort aims to better represent variation in human reference genome, Genome Web (11 pages).
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Truszkowski, 2011, New developments on the cheminformatics open workflow environment CDK-Taverna, J Cheminform 3:54.
Turi, 2007, Taverna Workflows: Syntax and Semantics, IEEE Int Conf on e-Science and Grid Computing 441-448.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Wassink, 2009, Using R in Taverna: RShell v1.2. BMC Res Notes 2:138.
Waterman, 1976, Some biological sequence metrics, Adv Math 20(3):367-387.
Wellcome Trust Case Control Consortium, 2007, Genome-wide association study of 14,000 cases of seven common diseases and 3,000 shared controls, Nature 447:661-678.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Abouelhoda, 2012, Tavaxy: integrating Taverna and Galaxy workflows with cloud computing support, BMC Bioinformatics 13:77.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar 2013, Haplotype assembly in polyploid genomes and identical by descent shared tracts, BioInformatics 29(13):352-i360.
Airoldi, 2008, Mixed membership stochastic blockmodels, JMLR 9:1981-2014.
Altera, 2007, Implementation of the Smith-Waterman algorithm on reconfigurable supercomputing platform, White Paper ver 1.0 (18 pages).
Altschul, 1986, Optimal Sequence Alignment Using Athne Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioninformatics 29(10):1250-1259.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages); retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.
Chen, 2012, Transient hypermutability, chromothripsis and replication-based mechanisms in the generation of concurrent clustered mutations, Mutation Res 750(1):562-59.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1:e167.
Cohen-Boulakia, 2014, Distilling structure in Taverna scientific workflows: a refactoring approach, BMC Bioinformatics 15(Suppl 1):S12.

(56) References Cited

OTHER PUBLICATIONS

Compeau, 2011, How to apply de Bruijn graphs to genome assembly, Nat Biotech 29(11):987-991.
Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Dudley, 2009, A quick guide for developing effective bioinformatics programming skills, PLoS Comput Biol 5(12):e1000589.
Durham, 2005, EGene: a configurable pipeline system for automated sequence analysis, Bioinformatics 21(12):2812-2813.
Enedelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with Air, Genome Res 15:54-66.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Glusman, 2014, Whole-genome haplotyping approaches and genomic medicine, Genome Med 6:73, Mar. 19, 2018.
Goto, 2010, BioRuby: bioinformatics software for the Ruby programming language, Bioinformatics 26(20):2617-2619.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harenberg, 2014, Community detection in large-scale networks: a survey and empirical evaluation, WIREs Comp Stat 6:426-439.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, A survey of sequence alignment algorithms for next-generation sequencing, Briefings in Bionformatics 11(5):473-483.
Life Technologies, 2013, Rapid Exome Sequencing Using the Ion Proton System and Ion Ampliseq Technology, Application Note (5 Pages).
Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6(4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.

(56) References Cited

OTHER PUBLICATIONS

Nenadic, 2010, Nested Workflows, the Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Rawe, 2013, Low Concordance of Multiple Variant-Calling Pipelines: Practical Implications for Exome and Genome Sequencing, Genome Med 5:28.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation: Practice and Experience 18(10):1067-1100.
Oshlack, 2010, From RNA-seq reads to differential expression results. Genome Bio 11:220.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Peixoto, 2014, Efficient Monte Carlo and greedy heuristic for the inference of stochastic block models, Phys. Rev. E 89, 012804.
Pope, 2014, ROVER Variant Caller: Read-Pair Overlap Considerate Variant-Calling Software Applied to PCR-Based Massively Parallel Sequencing Datasets, Source Code Bio Med 9:3.
Posada, 1998, MODEL TEST: testing the model of DNA substitution, Bioinfomiatics 14(9):817-8.
Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Wu, 2010, Fast and SNP-tolerant detection of complex variants and splicing in short reads, Bioinformatics, 26(7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yang, 2014, Community detection in networks with node attributes, proc IEEE ICDM '13, arXiv:1401.7267.
Yanovsky, 2008, Read mapping algorithms for single molecule sequencing data, Proc 8th Int Workshop Alg Bioinformatics 5251:38-49.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Yu, 2010, The construction of a tetraploid cotton genome wide comprehensive reference map, Genomics 95:230-240.
Zhang, 2013, Taverna Mobile: Taverna workflows on Android, EMBnet J 19(B):43-45.
Zhao, 2012, Why Workflows Break-Understanding and Combating Decay in Taverna Workflows, eScience 2012, Chicago, Oct. 2012.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Hokamp, 2003, Wrapping up BLAST and Other Applications for Use on Unix Clusters, Bioinformatics 19(3)441-42.
Holland, 2008, BioJava: an open-source framework for bioinformatics, Bioinformatics 24(18):2096-2097.
Homer, 2010, Improved variant discovery through local re-alignment of short-read next generation sequencing data using SRMA, Genome Biol 11(10):R99.
Hoon, 2003, Biopipe: A flexible framework for protocol-based bioinformatics analysis, Genome Res 13(8):1904-1915.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hull, 2006, Taverna: a tool for building and running workflows of services, Nucl Acids Res 34(Web Server issue): W729-32.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated May 5, 2016, for International Patent Application No. PCT/US2016/020899, wiht International Filing Date Mar. 4, 2016 (12 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014 (22 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201, with International Filing Date May 19, 2016 (14 pages).
International Search Report and Written Opinion dated Sep. 7, 2016, for International Application No. PCT/US2016/036873, with International filing date Jun. 10, 2016 (8 pages).
International Search Report and Written Opinion in the International Searching Authority dated Nov. 17, 2015, for International Application No. PCT/US2015/048891, (11 Pages).
Kano, 2010, Text mining meets workflow: linking U-Compare with Taverna, Bioinformatics 26(19):2486-7.
Katoh, 2005, MAFFT version 5: improvement in accuracy of multiple sequence alignment, Nucl Acids Res 33(2):511-518.
Kawas, 2006, BioMoby extensions to the Taverna workflow management and enactment software, BMC Bioinformatics 7:523.
Kehr, 2014, Genome alignment with graph data structures: a comparison, BMC Bioinformatics 15:99.

(56) References Cited

OTHER PUBLICATIONS

Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
Kumar, 2010, Comparing de novo assemblers for 454 transcriptome data, BMC Genomics 11:571.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol. 10:R25.
Lanzen, 2008, The Taverna Interaction Service: enabling manual interaction in workflows, Bioinformatics 24(8)1118-20.
Larkin, 2007, Clustal W and Clustal X version 2.0, Bioinformatics 23(21):2947-2948.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, MOSAIK: A hash-based algorithm for accurate next-generation sequencing short-read mapping, PLoS One 9(3):e90581.
LeGault, 2010, Learning Probalistic Splice Graphs from RNA-Seq data, pages.cs.wisc.edu/~legault/cs760_writeup.pdf; retrieved from the Internet on Apr. 6, 2014.
LeGault, 2013, Inference of alternative splicing from RNA-Seq data with probabilistic splice graphs, Bioinformatics 29(18):2300-2310.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Denoeud, 2004, Identification of polymorphic tandem repeats by direct comparison of genome sequence from different bacterial strains: a web-based resource, BMC Bioinformatics 5:4 pp. 1-12.
Duan et al., Optimizing de novo common wheat transcriptome assembly using short-read RNA-Seq data. (2012) pp. 1-12, vol. 13, BMC Genomics.
Durbin, 2014, Efficient haplotype matching and storage using the positional Burrows-Wheeler transform (PBWT), Bioinformatics 30(9):1266-1272.

Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Gerlinger, 2012, intratumor Heterogeneity and Branched Evolution Revealed by Multiregion Sequencing, 366:10 883-892.
Grasso, 2004, Combining partial order alignment and progressive multiple sequence alignment increases alignment speed and scalability to very large alignment problems, Bioinformatics 20(10):1546-1556.
International Search Report and Written Opinion dated Aug. 31, 2017, for International Application No. PCT/US2017/018830 with International Filing Date Feb. 22, 2017, (11 pages).
International Search Report and Written Opinion dated Apr. 19, 2017 for International Patent Application No. PCT/US2017/012015, (14 Pages).
International Search Report and Written Opinion dated Jan. 10, 2017, for International Patent Application No. PCT/US16/57324 with International Filing Date Oct. 17, 2016, (7 pages).
International Search Report and Written Opinion dated Apr. 7, 2017, for International Patent Application No. PCT/US17/13329, filed Jan. 13, 2017, (9 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, PCT/US2014/060690 (11 pages).
Koolen, 2008, Clinical and Molecular Delineation of the 17q21.31 Microdeletion Syndrome, J Med Gen 45(11):710-720.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2014, Accurate read mapping using a graph-based human pan-genome, ASHG 2014 Abstracts.
Lupski, 2005, Genomic disorders: Molecular mechanisms for rearrangements and conveyed phenotypes, PLoS Genetics 1(6):e49.
Marth et al., 1999—A general approach to single-nucleotide polymorphism discovery, pp. 452-456, vol. 23, Nature Genetics.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Parks, 2015, Detecting non-allelic homologous recombination from high-throughput sequencing data, Genome Biol 16:17.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Sturgeon, RCDA: a highly sensitive and specific alternatively spliced transcript assembly tool featuring upstream consecutive exon structures, Genomics, Dec. 2012, 100(6): 357-362.
Sudmant, 2015, An integrated map of structural variation in 2,504 human genomes, Nature 526:75-81.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Written Opinion issued in SG 11201601124Y.
Written Opinion issued in SG 11201602903X.

(56) References Cited

OTHER PUBLICATIONS

Written Opinion issued in SG 11201603039P.
Written Opinion issued in SG 11201603044S.
Written Opinion issued in SG 11201605506Q.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.

* cited by examiner

SYSTEMS AND METHODS FOR GENOTYPING WITH GRAPH REFERENCE

TECHNICAL FIELD

The invention relates to medical genetics and the analysis of genetic data.

BACKGROUND

Genotyping is the process of characterizing genetic variations in an individual, population, or ecological sample. Genotyping has typically been performed by performing biological assays and comparing the results to a reference genome, e.g., by restriction fragment length polymorphism identification (RFLPI) of genomic DNA, polymerase chain reaction (PCR), and DNA sequencing. More recently, genotyping has been transformed by the development of next-generation sequencing (NGS) technologies. The standard approach to variant discovery and genotyping from NGS data has been to map NGS sequence reads to a linear reference genome to identify positions where the sample contains variations.

Mapping NGS reads to a linear reference genome has limitations. First, the sample may contain sequences absent or divergent from the reference genome, e.g., through horizontal transfer events in microbial genomes, or at highly diverse loci, such as the classical HLA genes. In those cases, short reads either cannot or are unlikely to map correctly to the reference. Second, reference sequences (particularly of higher eukaryotes) are often incomplete, notably in telomeric and pericentromeric regions. Reads from missing regions will often map, sometimes with apparently high certainty, to paralogous regions, potentially leading to false variant calls. Third, methods for variant calling from mapped reads typically focus on a single variant type. However, where variants of different types cluster, focusing on a single type can lead to errors, for example, through incorrect alignment around indel polymorphisms. Fourth, although there are methods for detecting large structural variants, these cannot determine the exact location, size, or allelic sequence of variants. Finally, NGS mapping approaches typically ignore prior information about genetic variation within the species.

SUMMARY

The invention provides genomic references structured as reference graphs that can store genetic sequences from multiple organisms and that are transformed into traversal graphs that represent diploid genotypes of organisms. A reference graph includes nodes connected by edges in which the edges represent sequence data. A path through a series of connected nodes and edges represents a genetic sequence from a chromosome of an organism. Genetic variation within a diploid organism, within a population, or both, may be represented by multiple paths through a reference graph. The reference graph may be transformed into a traversal graph.

A traversal graph includes nodes connected by edges in which a path through the edges represents a diploid genotype. Genetic analysis using the traversal graph takes advantage of relationships between two different haploid genotypes in diploid organisms. Two separate haploids may be naturally related such that determining that one of the haploids traverses a specific branch of the reference graph gives information about the probability that the other haploid traverses certain branches. A simple example would be for a mutation known to be lethal when homozygous. When reads from a living organism traverse a branch from the reference graph corresponding to that mutation, it is highly probably that at least some reads from that organism will traverse another branch at that locus. The traversal graph represents valid diploid genotypes and evidence is used to assign scores or weights to edges in the traversal graph to indicate a likelihood of the genotypes. Use of the traversal graph allows an organism's diploid genotype to be elucidated (e.g., by mapping NGS sequence reads to the reference graph, assigning scores to corresponding branches of the traversal graph, and selecting the path through the traversal graph with the best score). Since the reference graph represents genetic variation across populations, sequence reads from a subject may be analyzed against all known alleles and indels to correctly identify each haploid genotype in the subject. Since edges in the traversal graph represent diploid genotypes and edge weights represent probabilities of those diploid genotypes, a diploid genotype for the subject may be identified and reported by following the highest-weighted path through the traversal graph, as given by mapping the reads to the corresponding reference graph. Since the true diploid genotype may be reported by mapping reads to the reference graph and following the highest-scoring corresponding path through a traversal graph, the analysis of genetic information such as sequence reads is uncoupled from the narrow perspective imposed by the use of a linear reference.

In certain aspects, the invention provides methods of determining a genotype of an organism. Methods include providing a reference graph comprising nodes connected by edges into a plurality of paths—the plurality of paths including a first path representing a first haplotype A and a second path representing a second haplotype B—and identifying one or more genotypes corresponding to either of both of the first haplotype A and the second haplotype B. Methods further include assigning, based on genetic information from the organism, scores to the one or more identified genotypes and identifying a genotype having a highest score in the assigning step, thereby providing the genotype. The genetic information from the organism may include a plurality of sequence reads. The reference graph may be provided within a tangible memory subsystem of a hardware computer system, and the steps may be performed using a processor of the computer system, the processor coupled to the tangible memory subsystem. Preferably the nodes connected by the edges are stored in the tangible memory subsystem using adjacency lists comprising pointers to physical locations in the memory. In some embodiments, the assigning and following steps are performed using dynamic programming, e.g., using by using a shortest path algorithm, such as Dijkstra's algorithm.

In preferred embodiments, the identified genotypes include a first genotype AA, a second genotype AB, and a third genotype BB. Preferably, a method of the invention includes representing the first genotype AA, the second genotype AB, and the third genotype BB using a traversal graph comprising nodes connected by edges into a plurality of paths, the plurality of paths including a first traversal path representing the first genotype AA, a second traversal path representing the second genotype AB, and a third traversal path representing the third genotype BB. The method may further include determining weights for the first traversal path, the second traversal path, and the third traversal path based on numbers of the sequence reads that map to those paths. Identifying which of the first genotype AA, the second genotype AB, and the third genotype BB has the highest score relative to a reference may be done using dynamic programming (e.g., using Dijkstra's algorithm) to determine a most probable path through the traversal graph.

In some embodiments, A represents an allele of a gene known to be dominant and B represents an allele of the gene known to be recessive. Where the organism is a patient, the method may include providing a report for the patient that provides genotype analysis.

Aspects of the invention provide systems for determining a genotype of a subject. A preferred system has a reference graph stored therein, the reference graph comprising nodes connected by edges into a plurality of paths, the plurality of paths including a first path representing a first haplotype A and a second path representing a second haplotype B. The system also has instructions stored therein that when executed by the system cause the system to: identify one or more genotypes corresponding to either or both of the first haplotype A and the second haplotype B, assign—based on genetic information from the organism—scores to the one or more identified genotypes, and identify a genotype having a highest score in the assigning step, thereby providing the genotype. The genetic information from the organism may include a plurality of sequence reads. Preferably, the system includes a tangible memory subsystem wherein the reference graph is kept and a processor coupled to the tangible memory subsystem that executes the instructions. The nodes connected by the edges may be stored in the tangible memory subsystem using adjacency lists comprising pointers to physical locations in the memory. The assigning and identifying steps may be performed using dynamic programming using, e.g., Viterbi decoding. In preferred embodiments, the identified genotypes include a first genotype AA, a second genotype AB, and a third genotype BB. Preferably, the system represents the first genotype AA, the second genotype AB, and the third genotype BB using a traversal graph comprising nodes connected by edges into a plurality of paths, the plurality of paths including a first traversal path representing the first genotype AA, a second traversal path representing the second genotype AB, and a third traversal path representing the third genotype BB; and determines weights for the first traversal path, the second traversal path, and the third traversal path based on numbers of the sequence reads that map to those paths. Identifying which of the first genotype AA, the second genotype AB, and the third genotype BB has the highest score may include using dynamic programming to determine a most probable path through the traversal graph, e.g., via Dijkstra's algorithm.

BRIEF DESCRIPTION OF THE DRAWINGS

FIG. 12 shows the matrices that represent the comparison.

DETAILED DESCRIPTION

Systems and methods disclosed herein use reference graphs to store genetic sequences from multiple organisms. A reference graph includes nodes connected by edges in which the edges represent sequence data. A path through a series of connected nodes and edges in the reference graph represents a genetic sequence from a chromosome of an organism. Genetic variation within a diploid organism, within a population, or both, may be represented by multiple paths through a reference graph. The reference graph is transformed into a traversal graph that represents possible diploid genotypes of one or more organisms. A traversal graph includes nodes connected by edges in which a path through the edges represents a diploid genotype.

Genotyping Using Graph Data Structures

Some of the limitations in traditional methods can be addressed by genotyping using graph data structures. In a reference graph representation of a genome, such as a directed acyclic graph (DAG), genetic variations within species can be incorporated as divergent paths along the graph. Sequence reads map to edges or paths through the reference graph, and then genotyping can be performed by simply counting the number of reads across each path. Because the sequence reads are aligned to the reference graph which includes known variations, the subsequent step of identifying mutations by comparing to a table of known mutations can be eliminated. Further, alignment to reference graphs results in greatly improved results for larger structural variants, as well as indels and SNPs located near structural variants. Additionally, in some cases there may be no need to perform a variant calling step because an ideal reference graph will not have any mismatches from the sequence read (of course variant calling can still be performed to detect unknown variations).

Genotyping using graphs also allows for computational complexities and considerations. The present disclosure recognizes that genotyping using graphs can be performed by enumerating, in an interval between two nodes of the reference graph connected by edges representing possible haplotypes, the possible genotypes from the possible haplotypes; scoring each of the genotypes based on a plurality of observed sequence reads mapped to each edge; and then using dynamic programming to determine the most likely genotype.

Figure 1:
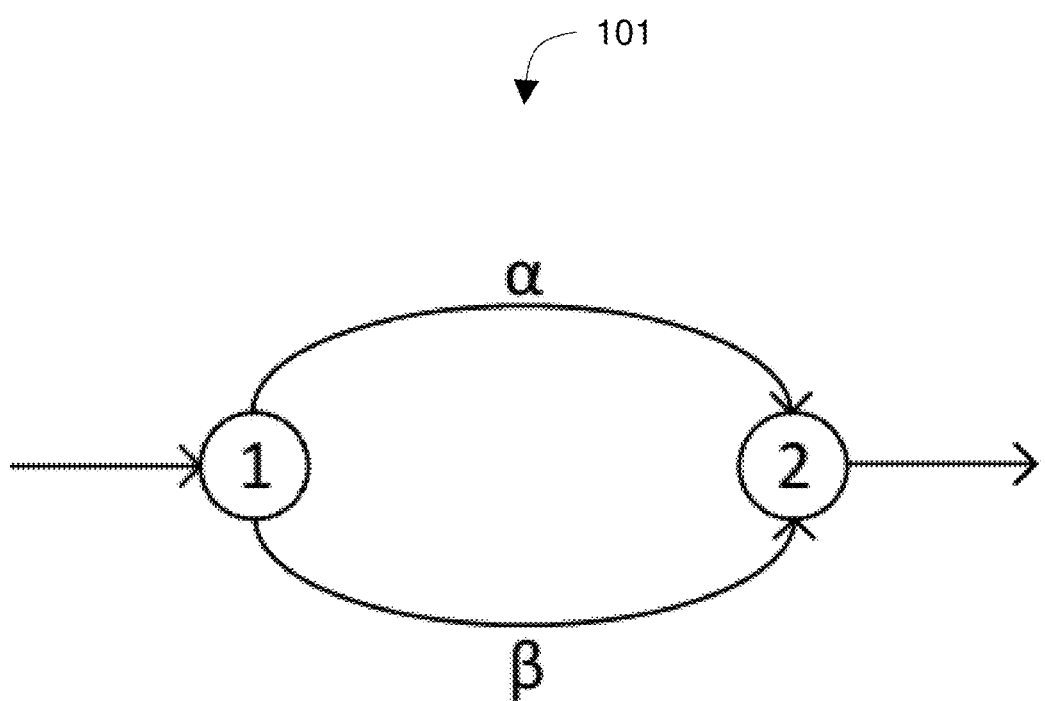
FIG. 1 shows a simple reference graph.

FIG. 1 shows a simple reference graph 101 having two paths α and β connecting nodes 1 and 2. The reference graph 101 is shown as a directed acyclic graph (DAG) and it may be preferable to use a directed graph to represent genetic information. Path α represents a SNP, whereas path β represents the canonical reference sequence. For an individual having two copies of each chromosome (i.e., two haploids), the individual's diploid genotype may be selected from one of three possible states: αα (both chromosomes include α), αβ (only one chromosome includes α), or ββ (no variation).

Identifying the most likely state or genotype can be performed by considering the weight of evidence provided by genetic information from an organism. Any suitable type of genetic information from the organism may be used. In some embodiments, the genetic information from the organism is provided by an alignment file containing mapped sequencing reads. (Such evidence can include various properties of mapped sequence reads, such as position on a reference genome or graph; the number of mapped sequence reads at a given position; and qualities of mapped sequence reads, such as individual base quality, mapping quality, and the like.) One approach is to identify the two most probable paths in the reference graph 101, which reflect the two most probable genotypes. However, this problem becomes more complicated by the fact that the two most probable paths have a relationship between them. Two separate haploids may be naturally related such that determining that one of the haploids traverses a specific branch of the reference graph gives information about the probability that the other haploid traverses certain branches. A simple example would be for a mutation known to be lethal when homozygous. When reads from a living organism traverse a branch from the reference graph corresponding to that mutation, it is highly probably that other reads from that organism traverse a branch that does not include the mutation. Thus in a sense, two separate haploids have knowledge of one another; the act of one of a pair of haploids traversing a branch may change the probability of the second of the pair traversing that branch. Normally, this is a problem that is difficult to overcome. It is noted that in the case of a reference graph, all paths typically converge back to a base or reference branch, representing the canonical reference sequence (e.g., the hg38 reference genome). Methods of the invention may be used to leverage the property of a pair haploids by which traversal of a branch by one of the pair may change the probability of the second of the pair traversing that branch. In this example, that property can be leveraged to represent the states of all possible genotypes as nodes in a separate graph. That separate graph is here referred to as a traversal graph because each edge in the traversal graph represents a state of two haploids, i.e., a pair of edges traversed by two haploids in a reference graph. The traversal graph represents all possible valid states for possible genotypes in the reference graph.

Figure 2:
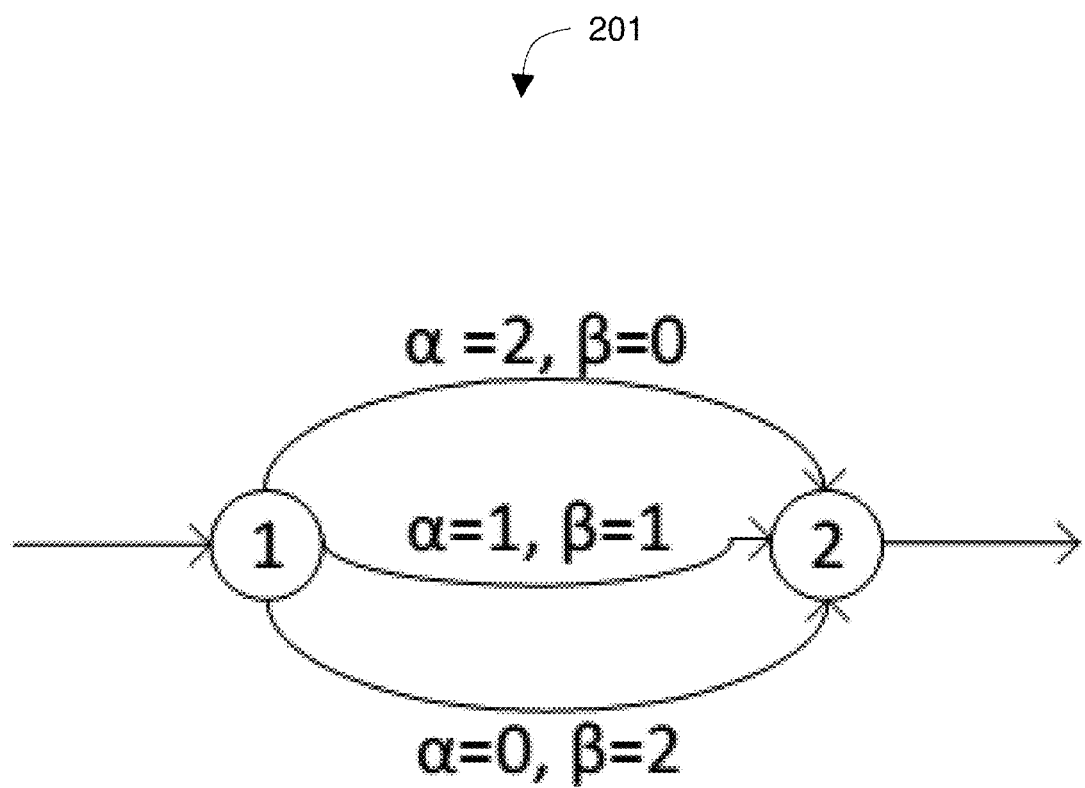
FIG. 2 shows an embodiment of a traversal graph representing the possible states of the reference graph.

FIG. 2 shows a traversal graph 201 representing the possible states of the reference graph 101. The traversal graph 201 has the first and second nodes connected by three edges, each edge representing a possible state of the possible diploid genotypes possible from the reference graph 101, i.e., αα, αβ, and ββ. In other words, the traversal graph identifies all possible states of genotypes between the first and second nodes in the reference graph. Genotyping now becomes identifying which path through the traversal graph 201 is the most likely path for a particular organism, e.g., by considering evidence in the form of sequence reads in an alignment file mapping to edges in the reference graph 101.

Figure 3:
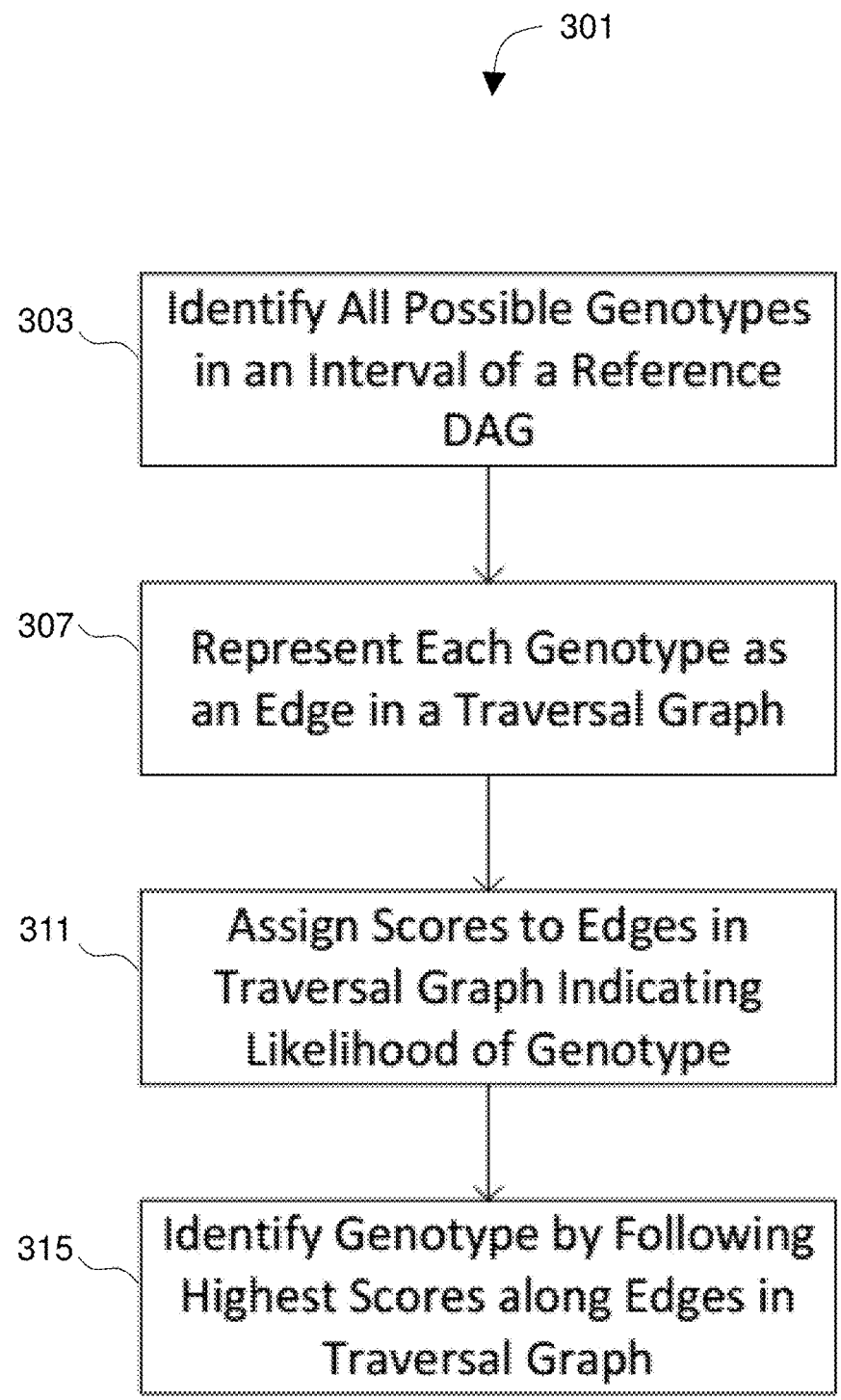
FIG. 3 diagrams a method of genotyping using a graph data structure.

FIG. 3 diagrams a method 301 of genotyping using a graph data structure. At a high level, the method 301 includes identifying 303 all possible genotypes in an interval of a reference graph. An interval can refer to a region in a reference graph in which there are at least two paths (e.g., by a pair of edges or vertices) representing variation from a reference sequence. For example, an interval can begin at a transition point in which two branches diverge from a node, and end at a transition point in which two branches rejoin at a node. Similarly, an interval can span a region in which there are a plurality of overlapping paths. However, an interval can also comprise a region between any two positions in a reference graph.

Assuming a single path through the reference graph (such as the reference graph 101 of FIG. 1) represents potential alleles along a single haploid chromosome, a diploid genotype will comprise a pair of paths through the reference graph. Each such possible diploid genotype is represented 307 as an edge in a traversal graph, and a full traversal graph is built by connecting the edges in a manner such that any path through the graph represents a possible full diploid genotype for an organism. Using some suitable technique (e.g., mapping sequence reads or correlating alleles to phenotypes), scores are assigned 311 to edges in the traversal graph indicating likelihoods of the corresponding genotype.

Evidence can be used to assign scores or weights to edges in the graph, thus indicating the likelihood of that genotype. For example, each of the states for the traversal graph 201 of FIG. 2 can be represented by a probability density function $\varphi_{\alpha\beta}$, having non-zero states $\varphi_{\alpha\beta}$ (2,0), $\varphi_{\alpha\beta}$ (1,1), and $\varphi_{\alpha\beta}$ (0,2) (wherein the integers in each tuple represent the number of chromosomes following each path). One may then assign the values of each probability density function for each state as weights to the edges in the graph, thus representing the probability of that genotype. The most likely genotype may then be selected based on the scores, i.e., by following 315 the highest scores along edges in the traversal graph. (Similarly, the scores may be negative logged such that genotyping may be performed by following the lowest scores. In both cases, the scores represent the likelihood of a particular genotype.)

A genotype can refer to the presence or absence of a single variation in one or both chromosomes. Accordingly, in the example above, a genotype refers to whether an individual has the genotype αα, αβ, or ββ. However, a genotype can also refer to the presence or absence of a plurality of variations in one or both chromosomes. Accordingly, once the probabilities have been set for a traversal graph representing multiple possible variations, one may use dynamic programming to identify the genotype for the plurality of variations by traversing the graph and following those edges with the highest probability. The single path having the highest probability yields the genotype for that individual. Thus, finding the highest scoring path through the traversal graph yields the genotype for a genomic sample, and is akin to finding two separate paths through the reference DAG.

Constructing a Traversal Graph

As noted above, each edge of a traversal graph can represent two haploid paths in a reference graph. Accordingly, a simple graph having two nodes connected by two edges (one edge representing the reference sequence β and the other edge representing a variant α), can be represented by a traversal graph having two nodes connected by three edges representing the possible genotype states of the reference graph.

However, constructing a traversal graph can be more complicated. As previously noted, genomic reference graphs typically comprise a base or backbone sequence representing the canonical genomic reference (e.g., GRCh38/hg38 for human; GRCm38/mm10 for mouse; CSAC 2.1.4/panTro4 for chimpanzee). Known variations, such as single nucleotide polymorphisms (SNPs), small insertions and deletions (indels), and larger structural variants (SVs) are represented as edges which provide a path that directs away from the backbone sequence and then reconnects at a later position. In complex regions of the graph with high variation, the number of possible genotypes in an interval increases due to the increased number of available combinations for two chromosomes.

Figure 4:
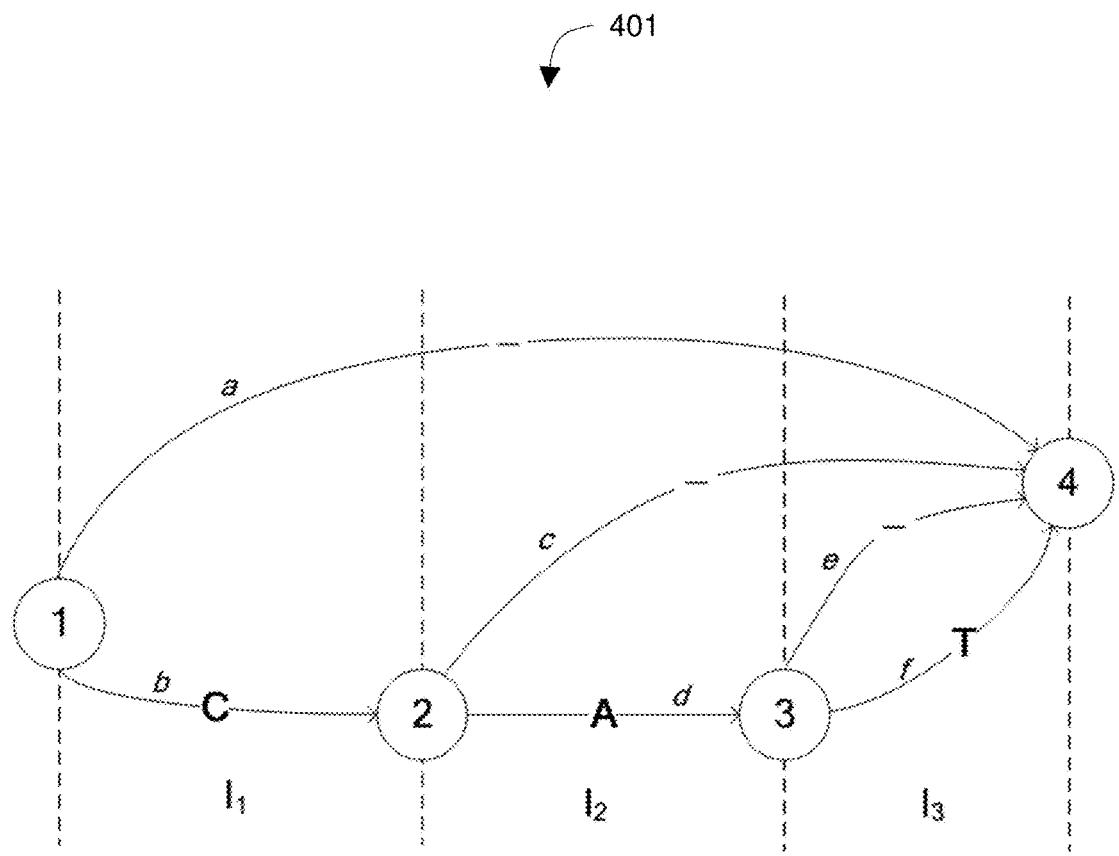
FIG. 4 shows a possible reference graph.

For example, FIG. 4 shows a subsection of a possible reference graph 401. In the reference graph 401, four positional nodes {1 . . . 4} are connected by six edges {a . . . f}. (When considered in the context of a genomic reference graph representing an entire genome, nodes 1 and 4 may be connected to additional nodes representing a backbone or reference sequence for that genome.) As shown in this embodiment, the first node (1) includes two outgoing edges representing either the backbone or reference sequence "C" which connects to the second node (2, and a deletion ("–") of three nucleotides reconnecting with the backbone at the fourth node (4). The second node (2) includes two outgoing edges representing the reference sequence "A" which connects to the third node (3), and a deletion ("–") of two nucleotides reconnecting with the backbone at the fourth node (4). Similarly, the third node (3) includes two outgoing edges representing the reference sequence "C" which connects to the fourth node (4), and a deletion ("–") of one nucleotide reconnecting with the backbone at the fourth node (4).

Four haploid paths may be taken through the graph 401. The reference sequence or backbone path is "CAT" (passing through the edges connecting nodes 1, 2, 3, and 4). Another path presents a deletion of the entire reference sequence ("–") (by traversing the edge connecting nodes 1 and 2). Another path represents a deletion of AT ("C–") (by traversing a path connecting nodes 1, 2, and 4), and the last available path represents a deletion of only the final T ("CA–") (by traversing an alternate path connecting nodes 1, 2, 3, and 4).

Between each positional node, we define an interval, such that the reference graph 401 has three intervals I∈{1,2,3}. All of the edges $\varepsilon_i$ overlapping each interval are identified, each of which represents a contribution to the reference genome. Each edge has a traversal value $t_i \in [0,1,2]$, which represents whether the edge can be traversed by 0, 1, or 2 of the chromosomes in a sample.

Figure 5:
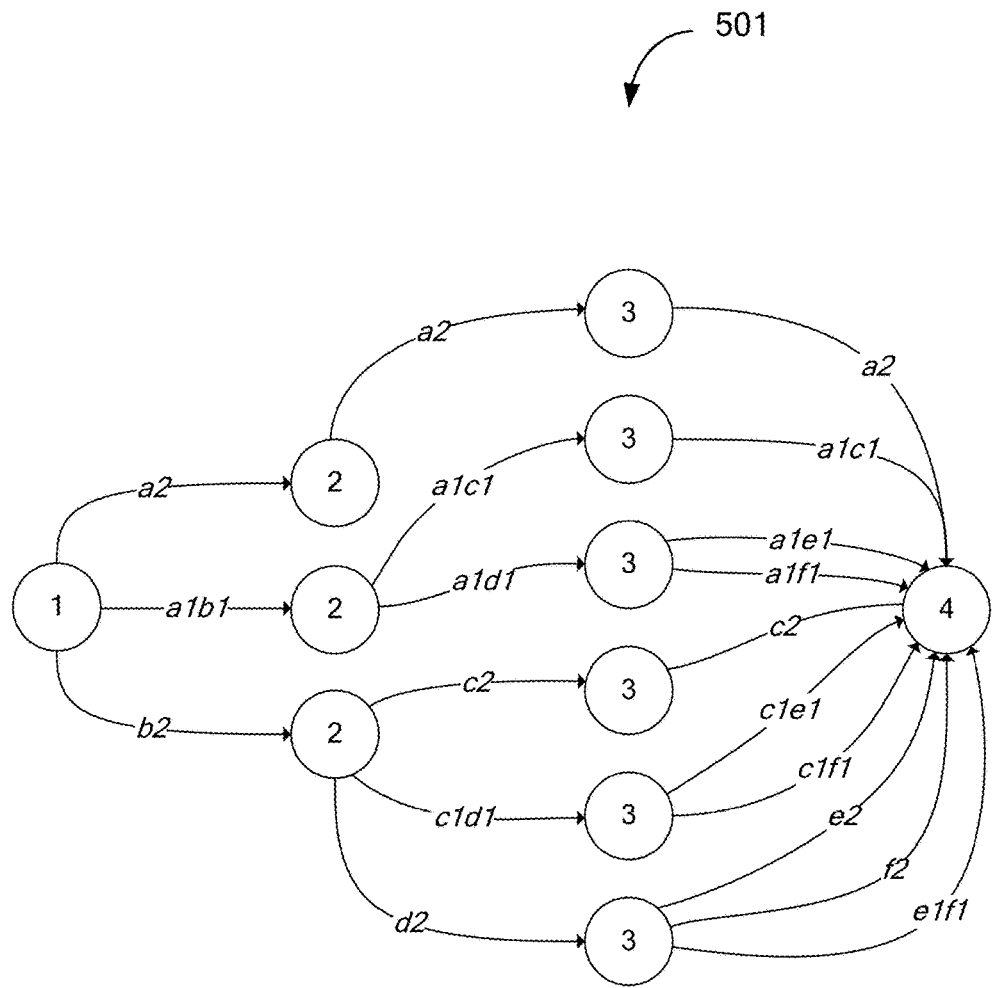
FIG. 5 gives a traversal graph built from the reference graph of FIG. 4.

Once all of the edges and traversal values have been collected, a traversal graph 501 may be constructed, as shown in FIG. 5. First, a state S of each interval is defined as a labelling of the t-values of these edges in a valid manner, i.e., S={$t_0$=0, $t_i$=1, . . . }, subject to the constraint that $\Sigma_i t_i$=2 (indicating that there may only be two possible taken paths in a genomic sample, representing each chromosome). For interval I1, the possible paths comprise a2, a1b1, and b2. For interval I2, the possible paths comprise a2, a1c1, a1d1, c2, c1d1, and d2. For interval I3, the possible paths comprise a2, a1c1, a1e1, a1f1, c2, c1e1, c1f1, e2, f2, and e1f1.

FIG. 5 gives a traversal graph 501 built from the reference graph 401. Each edge in the traversal graph 501 represents an edge {a . . . f} or combination of edges of the reference graph 401, and whether the edge or edges are followed by 1 or 2 of the chromosomes in the sample. In the example, there are four possible haplotypes (in the reference graph 401), leading to ten unique paths representing each possible genotype. Each genotype is represented by a single path through the traversal graph 501. The traversal graph may be built by enumerating the number of possible states in each interval, determining the possible combinations of states between intervals, and creating a graph having edges and nodes that provides paths which correctly convey these possible states. In this way, each path through the traversal graph represents a possible diploid genotype of an organism.

The traversal graph 501 of FIG. 5 can be generated from the reference graph 401 of FIG. 4 in the following manner. Begin with interval I1 in the reference graph 401, which has possible genotypes a2, a1b1, and b2. For each possible genotype, create a directed edge and associate the edge with the genotype. As each of these genotypes begins from the first node (1) in the graph 401, create a node representing the first node (1) in the graph 501 and connect each of these edges to this node. Thus, the traversal graph 501 indicates that there are three possible genotypes between the first node (1) and the second node (2).

The second interval I2 has 6 possible genotypes from the collected edges in the reference graph 401: a2, a1c1, a1d1, c2, c1d1, and d2. Similarly, create edges and associate each edge with one of these genotypes. However, in the reference graph 401, note that only certain genotypes from interval I2 may be combined with genotypes from interval I1. For example, there is no possible genotype a2 that may be combined with d2. Accordingly, to include only those possible genotypes in the traversal graph 501, create multiple second nodes (2) to connect those edges from intervals I1 and I2 such that each connected pair of edges represents a possible genotype across intervals I1 and I2. In this way, only possible genotypes are represented in the traversal graph 501.

This process may similarly be repeated for interval I3 (having 10 possible genotypes, as shown), creating multiple third nodes (3) to connect the edges from interval I2 with those from I3. Finally, each of the edges from interval I3 may reconnect with a single node (4), as each of the possible paths in the reference graph 401 of FIG. 4 converge back to the base branch after interval I3. Each possible pair of paths from node 1 to node 4 in the reference graph 401 is now represented by a single path through the traversal graph 401. Accordingly, the geometry of the traversal graph 501 is constructed such that invalid paths or combinations of paths in the reference graph 401 are omitted.

While not shown here, the traversal graph 501 may include additional nodes and edges corresponding to additional genotypes in the reference graph 401 (e.g., those genotypes represented by paths upstream or downstream of the reference graph 401). Once the traversal graph 501 has been constructed, genotyping can be performed by scoring each of the edges. Scoring can be performed by considering evidence provided by sequence reads aligned to edges in the reference graph 401, for example. The most likely path can then be determined by identifying the most likely or shortest path, e.g., by a dynamic programming approach. This can be performed in a variety of ways, of which the following is one example.

Setting Expected Probabilities for Each State

The alignment, or positioning, of next-generation sequencing reads on a reference genome is typically modelled using either a negative binomial distribution or a Poisson distribution. In this example, the latter is chosen. First, the expected probability of reads mapping to edges given each possible state S is determined. Assume that a sample of next-generation sequencing reads are randomly distributed (i.e., ignore any potential GC bias or other related effects). In a sample having coverage k with read length L, a read is expected to start every k/L bases. This observation can form the basis for predicting an expected number of reads N that should be observed in a region having length α. The expected number of reads N overlapping this region and the number of reads beginning in this region are counted. The reads overlapping must start within the distance L before this region, so the problem becomes finding the expected number of reads starting in an interval of L+α. According to the Poisson distribution, the expected number of reads N of length L at least partially overlapping an interval of length a in a sample of coverage K is:

$$N = \frac{(L+\alpha)K}{L} \quad (1)$$

Using Equation (1), the likelihood or probability of sequence reads mapping to each edge of a reference graph given each possible state can be determined. Given the length $\lambda_i$ of each branch (e.g., measured by the number of nucleotides in the branch), the average length L of the sequence reads, and the t-values for each state ($S=\{t_0=0, t_1=1, \ldots\}$), the expected probabilities for the distribution of sequencing reads along each path can be defined in vector form:

$$\overline{p} \mid \lambda_1, \lambda_2, \ldots \lambda_N; t_1, t_2, \ldots, \quad (2)$$

$$t_N = \frac{\delta_{2,t_1+t_2+\ldots t_N}}{\sum_i t_i(L+\lambda_i)}(t_1(L+\lambda_1), t_2(L+\lambda_2), \ldots, t_N(L+\lambda_N))$$

(Note that the factor K/L from Equation (1) above is cancelled out from each dimension.)

In practical use, the vector simplifies considerably for all valid states. There will either be 1 or 2 non-zero terms, depending on whether the edge state is homozygous or heterozygous (i.e., there is only one edge with $t_i=2$, or two with $t_i=1$, $t_j=1$. This is due to the implicit assumption that reads cannot map from elsewhere to these edges. Consequently, the actual vector is tunably perturbed so as to give the zero states a small probability.

Figure 6:
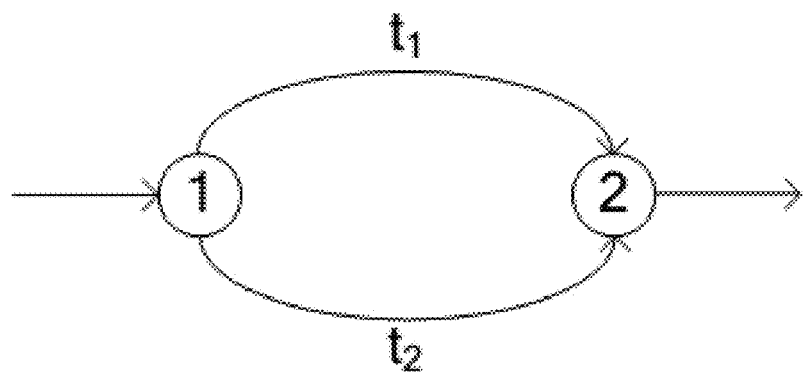
FIG. 6 shows a single reference graph and a corresponding traversal graph.
Figure 6:
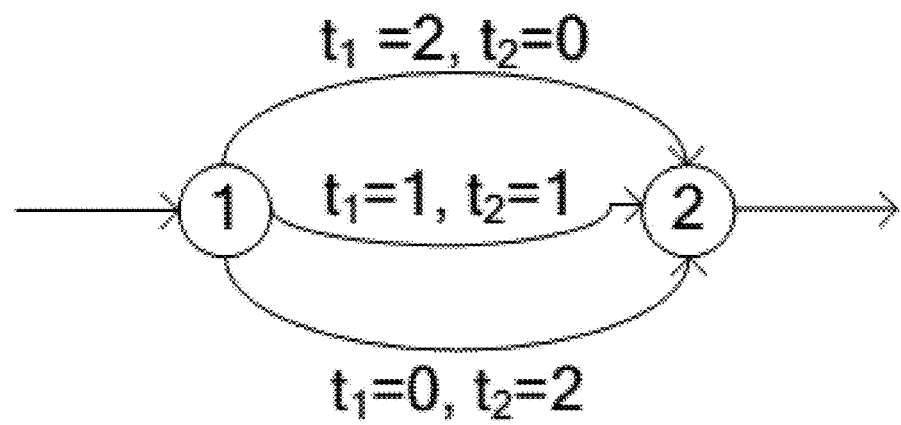

FIG. 6 shows a single reference graph 601 and a corresponding traversal graph 605. In the depicted reference graph 601, path $t_1$ may be 50 base pairs long and path $t_2$ may be 30 base pairs long. Given a sequence read length of 100 base pairs, the probability vector for state $\{t_1=2, t_2=0\}$ is $\{0, 1\}$; $\{t_1=1, t_2=1\}$ is $\{0.454, 0.545\}$; and $\{t_1=0, t_2=2\}$ is $\{0, 1\}$.

Identifying Weights for Traversal Graph Based on Evidence

The expected probabilities for each state can be compared with those exhibited by the evidence, i.e., the actual aligned sequence reads in an alignment file. For example, Bayes Theorem may be used to determine the probability of a particular state S given a set of aligned sequence reads R:

$$P(S \mid R) = \frac{P(S)P(R \mid S)}{P(R)} \quad (3)$$

(In certain examples, a learned prior probability for the state may be incorporated, but in the disclosed model this is not used.) Abbreviating Equation (3) yields $P(S|R) \propto P(R|S)$. A normalized version of this abbreviation may be used to determine the probability of each of the valid states for a given interval, i.e., the most likely genotype of a sample:

$$P(S) \propto \Pi_i p_i^{N_i} \quad (4)$$

where $p_i$ is from the vector given by Equation (2), and $N_i$ represents the number of sequence reads mapping to the corresponding edge. The term on the right hand side of Equation (4) may initially be addressed using a multinomial distribution stated in the following way. Imagine one is receiving aligned sequencing reads. The reads can map to one of the edges in a reference graph having several states. If the total number of aligned sequencing reads is large, the probability of a given state is given by Equation (4), with $p_i$ being the estimated proportion of reads for each edge given by Equation (2), and $N_i$ being the actual mapped number of reads drawn for each edge.

The result of P(S) will be higher for those states which are better supported by the evidence in the alignment file. The results for each state may then be assigned as scores for each genotype, such as by assigning weights to each edge of the traversal graph. To find the most likely genotype, the highest scoring edges are followed to obtain a single path which represents the genotype, e.g., by using dynamic programming. Similarly, the scores may be negative logged such that the lowest score represents the most likely genotype. The problem of genotyping then becomes finding the shortest path in the traversal graph, i.e., finding the path that minimizes the sum of the weights. Finding the shortest path according to weights in a graph is a well-known problem. Common algorithms for finding the shortest path include Dijkstra's algorithm, for example.

Dijkstra's algorithm and Viterbi's algorithm are examples of dynamic programming approaches that can be used to perform genotyping according to the disclosure. Dynamic programming refers to methods of solving a complex problem by breaking it down into a collection of simpler subproblems, solving each of those subproblems only once, and storing their solutions (also referred to as "memoization"). In this way, each memoized solution does not need to be re-solved the next time it is needed. Dynamic programming algorithms can be used for optimization, such as finding the shortest paths between two nodes in a graph. For example, Dijkstra's algorithm can be used to solve the shortest path problem in a successive approximation scheme. To apply Dijkstra's algorithm, use a computer system to let the node deemed to be a starting node be called the initial node. Let the distance of node Y be the distance from the initial node to Y. Under Dijkstra's algorithm, the computer system will assign some initial distance values and will try to improve them step by step. First, assign to every node a tentative distance value: set it to zero for our initial node and to infinity for all other nodes. Second, set the initial node as current. Mark all other nodes unvisited. Create a set of all the unvisited nodes called the unvisited set. Third, for the current node, consider all of its unvisited neighbors and calculate their tentative distances. Compare the newly calculated tentative distance to the current assigned value and assign the smaller one. For example, if the current node A is marked with a distance of 6, and the edge connecting it with a neighbor B has length 2, then the distance to B (through A) will be 6+2=8. If B was previously marked with a distance greater than 8 then change it to 8. Otherwise, keep the current value. Fourth, when all of the neighbors of the current node have been considered, mark the current node as visited and remove it from the unvisited set. A visited node will never be checked again. Fifth, if the destination node has been marked visited (when planning a route between two specific nodes) or if the smallest tentative distance among the nodes in the unvisited set is infinity (when planning a complete traversal; occurs when there is no connection between the initial node and remaining unvisited nodes), then stop. The algorithm has finished. Sixth and finally, otherwise, select the unvisited node that is marked with the smallest tentative distance, set it as the new "current node", and go back to the third step. More information regarding the use of Dijkstra's algorithm in a dynamic programming context can be found in Sniedovich, 2006, Dijkstra's algorithm revisited: the Dynamic Programming Connexion, Control and Cybernetics 25(3), the contents of which are incorporated by reference.

Incorporating Mapping Qualities

In some embodiments, mapping qualities from the sequence read alignment are incorporated. For example, a large number of low quality mappings to an edge should be less persuasive than a smaller number of reads mapping to a location with high precision. This can be added to the state probabilities as suggested by the multinomial distribution in Equations (3) and (4):

$$P(t_1,t_2,\ldots t_N|\text{reads})=\Pi_i^{N_i} p_i|\lambda_1,\lambda_2,\ldots \lambda_N; t_1, t_2, \ldots t_N^{N_i}, \quad (5)$$

where $N_i$ is the number of reads mapped to each edge, and $p_i$ (as defined by Equation (2)) are approximated. Approximating $p_i$, comprises sampling reads from each edge such that each read is sampled proportional to the mapping quality of each read. The state probabilities may then be averaged over these samplings. Other measures of mapping quality and read quality could also be used. For example, individual base call qualities (e.g., Phred scores) could be incorporated, or the number of bases a given read has that overlap a given branch.

Additional Methods

As previously noted, methods of genotyping according to the disclosure can identify the most likely genotype for a genomic sample using a variety of dynamic programming techniques. Dynamic programming is a method for solving a complex problem by breaking it down into a collection of smaller problems, solving the smaller problems once, and then storing their solutions. In this way, methods according to the disclosure score each possible subset of a full genotype, and then select the most likely full genotype by subsequently evaluating the scores. For the simple SNP example given above, this can comprise simply evaluating the most likely genotype from those available. However, for more complex situations (such as the multiple deletion example above) and for genotyping larger portions of the reference graph comprising multiple consecutive positional nodes, a dynamic programming algorithm, such as Dijkstra's algorithm, can be used to identify the most likely genotype.

However, the disclosure is not meant to be so limited. For example, another embodiment according to the disclosure employs a hidden state model instead of a traversal graph. In such a model, each possible diploid genotype in an interval represents a hidden state. Intervals are identified from the reference graph based on transition or branching positions in which branches diverge from or rejoin nodes. The observations in the model would be the mapping configurations (e.g., positions, quality) of sequence reads on that corresponding interval in the reference graph. The most likely hidden state (i.e., diploid genotype) may then be determined based on the emission probabilities (which are mapped to the edge lengths in the traversal graph) and can be calculated from the observations. Allowed transitions between states are deduced at the end of each interval and then the transition probabilities can be deduced by ensuring that the probabilities of allowed transitions sum to one. One could then use the Viterbi algorithm to identify the most probable sequence of hidden states based on the observations. The feature in common is the enumeration of the possible genotypes given a plurality of haplotypes from a reference graph, scoring each of the genotypes based on a plurality of observed sequence reads mapped to each haplotype, and then determining the most likely genotype. For genotypes including a plurality of variations, dynamic programming can be used to determine the most likely genotype. For example, the Viterbi algorithm is a dynamic programming algorithm for finding the most likely sequence of hidden states, called the Viterbi path that results in a sequence of observed events, especially in the context of Markov information sources and hidden Markov models. For background, see Stanke et al., 2006, AUGUSTUS: Ab initio prediction of alternative transcripts, Nucl Ac Res 34:w435-9; U.S. Pub. 2014/0025312; and U.S. Pub. 2013/0080068, each incorporated by reference.

Thus it can be seen that embodiments of the invention provide a method 301 of determining a genotype from a plurality of haplotypes. In one embodiment, the method includes using a reference graph having a plurality of vertices and a plurality of edges, the plurality of vertices including a first vertex and a second vertex, the plurality of edges including a first edge connecting the first vertex and the second vertex, and a second edge connecting the first vertex and the second vertex. The method further includes associating haplotypes in the plurality of haplotypes to respective edges in the plurality of edges, the associating comprising associating a first haplotype in the plurality of haplotypes to the first edge and a second haplotype in the plurality of haplotypes to the second edge; identifying 303 a plurality of genotypes from the plurality of haplotypes, the identifying comprising identifying a first genotype comprising the first haplotype, a second genotype comprising the first haplotype and the second haplotype, and a third genotype comprising the second haplotype; assigning 311 scores to each genotype of the plurality of genotypes, the scoring considering at least in part a plurality of sequence reads mapped to the plurality of edges; and selecting the most likely genotype from the plurality of genotypes based on the score for each genotype, for example, by following 315 highest scores along edges in the traversal graph.

In some embodiments, selecting the most likely genotype from the plurality of genotypes based on the score for each genotype further comprises using dynamic programming to determine the most likely genotype. Using dynamic programming to determine the most likely genotype may include using Viterbi decoding.

In certain embodiments of method 301, scoring each genotype of the plurality of genotypes comprises: associating the plurality of genotypes to a traversal graph, the traversal graph comprising a second plurality of vertices and a second plurality of edges, the plurality of vertices comprising a third vertex and a fourth vertex, the third vertex and fourth vertexes connected by a third edge, and fourth edge, and a fifth edge, the associating comprising associating the first genotype to the third edge, the second genotype to the fourth edge, and the third genotype to the fifth edge; and determining weights for each of the second plurality of edges at least in part by determining a first weight for the third edge based on a plurality of sequence reads mapped to the first edge, determining a second weight for the fourth edge based on a plurality of sequence reads mapped to the first edge and the second edge, and determining a third weight for the fifth edge based on a plurality of sequence reads mapped to the second edge. Selecting the most likely genotype from the plurality of genotypes based on the score for each genotype may include using dynamic programming to identify the most probable path through the traversal graph. Using dynamic programming to identify the most probable path may include using Dijkstra's algorithm.

Figure 7:
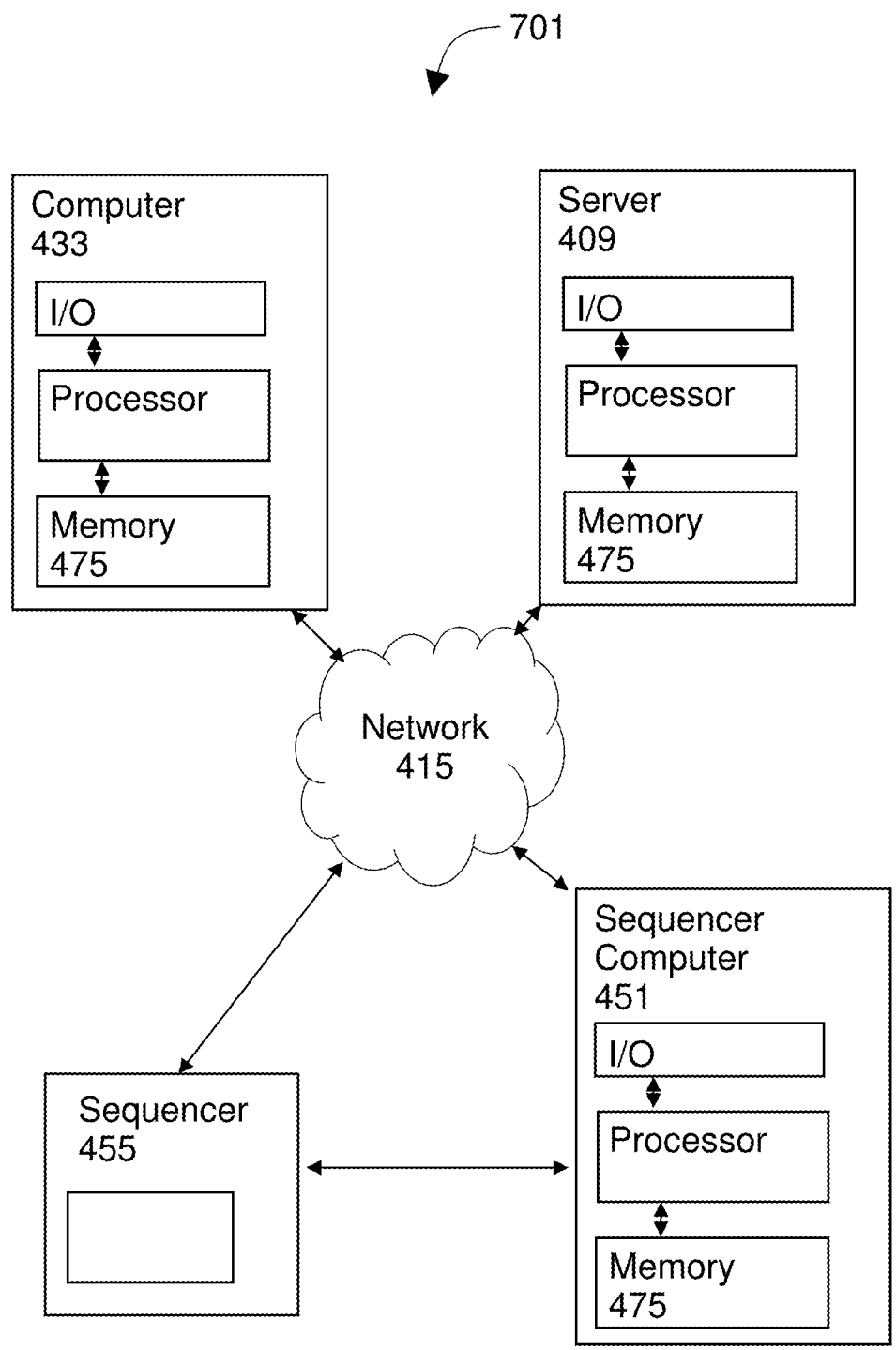
FIG. 7 illustrates a computer system for performing methods of the invention.

FIG. 7 illustrates a computer system 701 suitable for performing methods of the invention. The system 701 includes at least one computer 433. Optionally, the system 701 may further include one or more of a server computer 409 and a sequencer 455, which may be coupled to a sequencer computer 451. Each computer in the system 701 includes a processor coupled to a memory device and at least one input/output device. Thus the system 701 includes at least one processor coupled to a memory subsystem (e.g., a memory device or collection of memory devices 475). Using those mechanical components, the system 701 is operable to obtain a sequence generated by sequencing nucleic acid from a genome of a patient. In certain embodiments, the system uses the processor to transform known genomic sequences and variations into a reference graph. However, in other embodiments, the reference graph may be a previously existing graph and transferred to the system 701 by disk or network. Similarly, the system 701 may use the processor to: transform a reference graph into a traversal graph, such as the traversal graph 1215; enumerate possible diploid genotypes; score the diploid genotypes according to evidence in the form of aligned sequence reads; and use dynamic programming to determine a full genotype from the scored genotypes.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The memory subsystem 475 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 701 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Preferably, graphs according to the disclosure (such as reference graphs and traversal graphs) are stored in the memory subsystem 475 using adjacency lists or index-free adjacency, which may include pointers to identify a physical location in the memory subsystem 475 where each vertex is stored. In a preferred embodiment, the graph is stored in the memory subsystem 475 using adjacency lists. In some embodiments, there is an adjacency list for each vertex. For discussion of implementations see 'Chapter 4, Graphs' at pages 515-693 of Sedgewick and Wayne, 2011, Algorithms, 4th Ed., Pearson Education, Inc., Upper Saddle River N.J., 955 pages, the contents of which are incorporated by reference and within which pages 524-527 illustrate adjacency lists.

In certain embodiments, the system 701 performs operations in parallel. For example, portions of a reference graph can be split into separate graphs, and traversal graphs for each separate graph are then identified simultaneously in parallel using multiple processors. The traversal graphs are subsequently rejoined once the operations are complete. Similarly, other features, such as scoring genotypes based on mapped sequence reads, can be performed in parallel.

Figure 8:
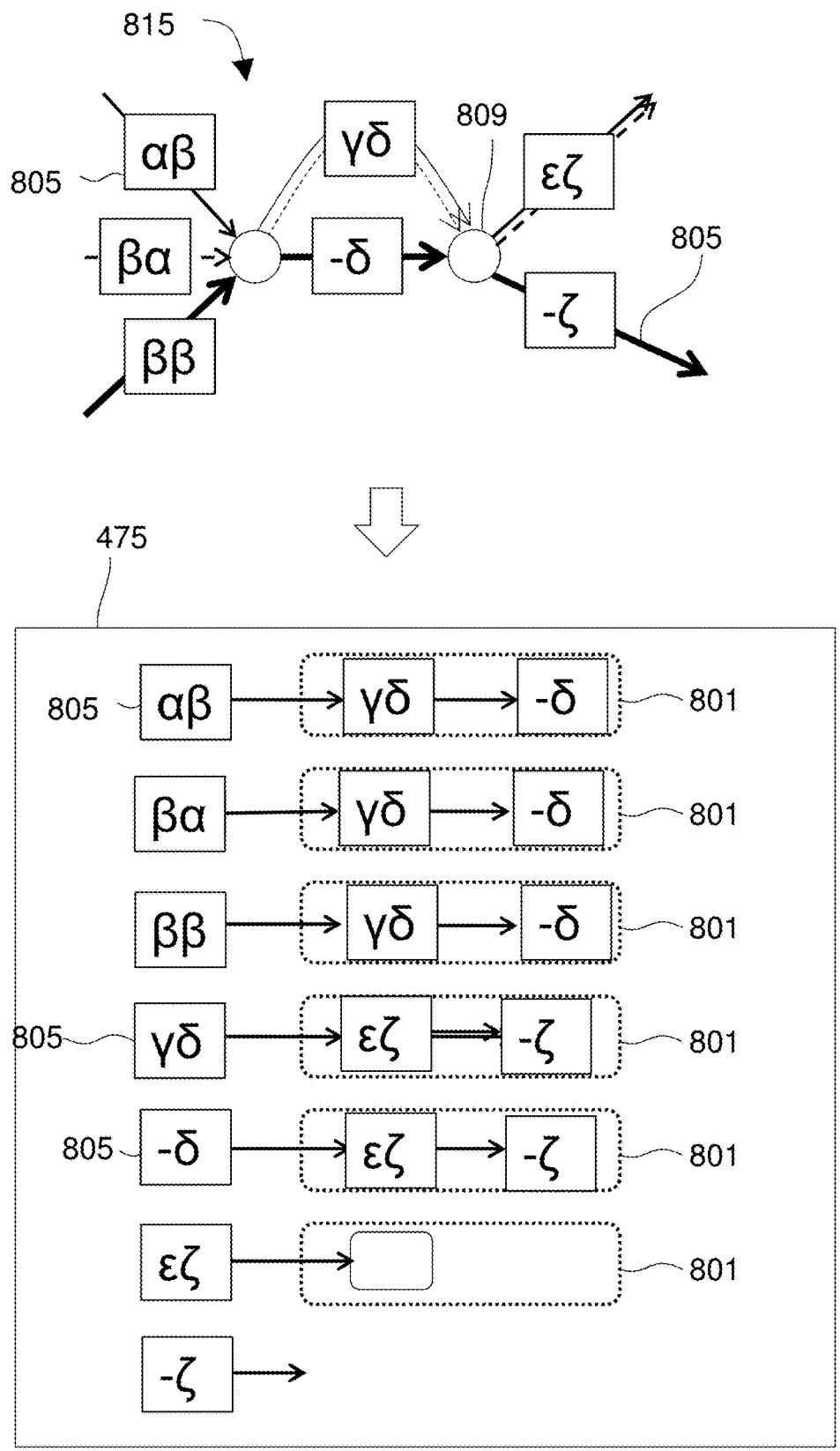
FIG. 8 shows the use of an adjacency list for each vertex.

FIG. 8 shows the use of an adjacency list 801 for each edge 805 in a graph, such as a hypothetical portion of a reference graph 815. The system 701 uses a processor to create the graph 815 that includes vertex objects 805 and edge objects 809 through the use of adjacency, i.e., adjacency lists or index free adjacency. Thus, the processor may create the graph 815 using index-free adjacency wherein an edge 805 includes a pointer to another edge 805 to which it is connected and the pointer identifies a physical location in on a memory device 475 where the connected vertex is stored. The graph 815 may be implemented using adjacency lists such that each vertex or edge stores a list of such objects that it is adjacent to. Each adjacency list comprises pointers to specific physical locations within a memory device for the adjacent objects. The graph 815 may be any of the reference graphs or traversal graphs shown herein and all such graphs may be stored using adjacency lists according to the strategems set out in FIGS. 8 and 9.

In the top part of FIG. 8, the graph 815 is illustrated in a cartoon-like visual-friendly format. The graph 815 will typically be stored on a physical device of memory subsystem 475 in a fashion that provide for very rapid traversals. In that sense, the bottom portion of FIG. 8 is not cartoon-like and represents that objects are stored at specific physical locations on a tangible part of the memory subsystem 475. Each edge 805 is stored at a physical location, the location of which is referenced by a pointer in any adjacency list 801 that references that node. Each edge 805 has an adjacency list 801 that includes every adjacent edge in the graph 815. The entries in the list 801 are pointers to the adjacent nodes.

In certain embodiments, there is an adjacency list for each vertex and edge and the adjacency list for a vertex or edge lists the edges or vertices to which that vertex or edge is adjacent. Similarly, each edge may be associated with a weight or score representing the likelihood of the diploid genotype represented by that edge.

Figure 9:
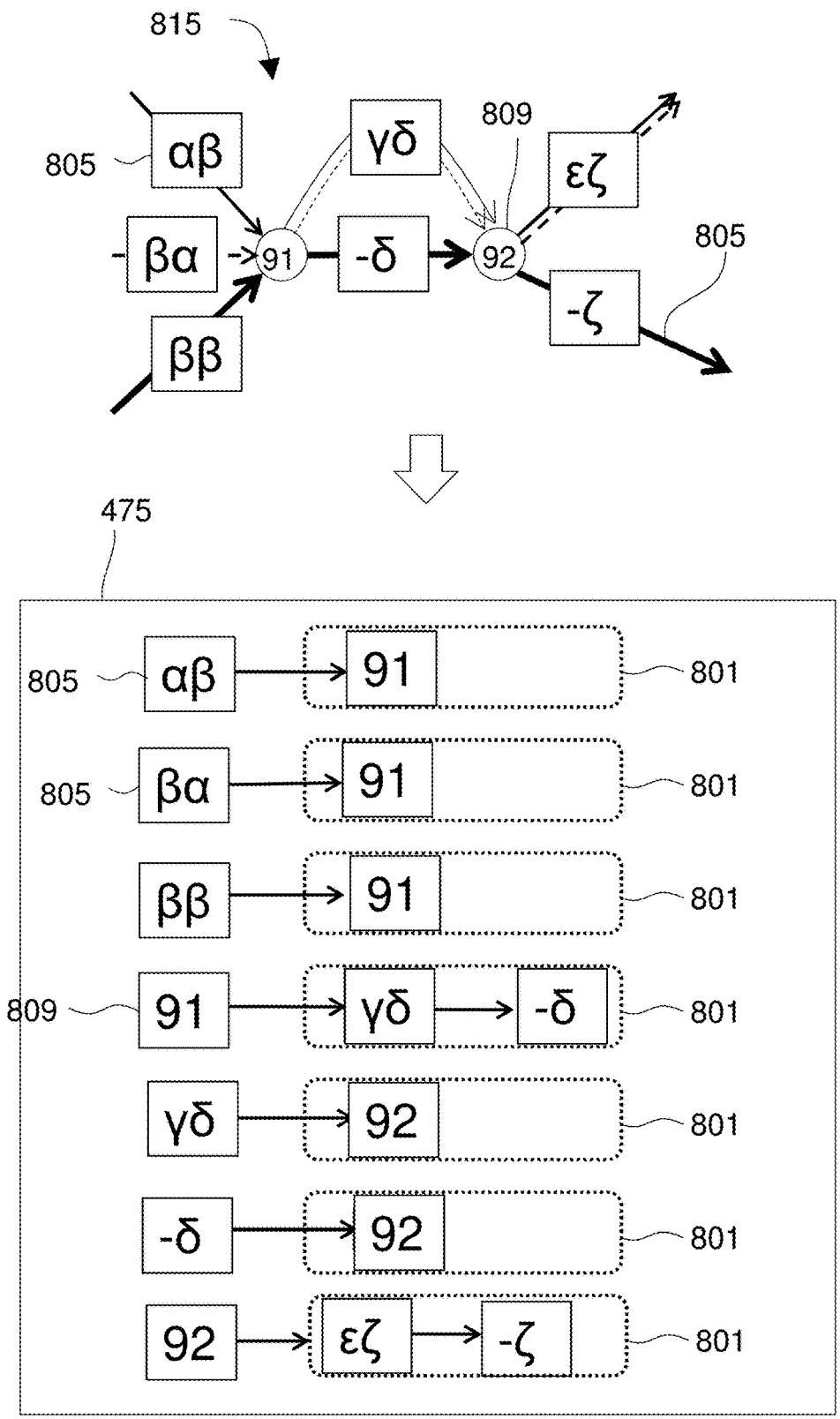
FIG. 9 shows the use of an adjacency list for each vertex and edge.

FIG. 9 shows the use of an adjacency list 801 for each edge 805 and node 809. As shown in FIG. 9, system 701 creates the graph 815 using an adjacency list 801 for each vertex and edge, wherein the adjacency list 801 for an edge 805 or node 809 lists the edges or vertices to which that vertex or edge is adjacent. Each entry in adjacency list 801 is a pointer to the adjacent vertex or edge. (Node and vertex are used synonymously.)

Preferably, each pointer identifies a physical location in the memory subsystem at which the adjacent object is stored. In the preferred embodiments, the pointer or native pointer is manipulatable as a memory address in that it points to a physical location on the memory and permits access to the intended data by means of pointer dereference. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph engine allows a sequence to be queried against a large-scale graph representing millions or billions of bases, using a computer system 701. Such a graph representation provides means for fast random access, modification, and data retrieval.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, each incorporated by reference), which obviates the need for index look-ups, allowing traversals (e.g., as done in the modified SW alignment operation described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described below). Specifically, index-free adjacency can be implemented such that the pointers contained within elements are references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale graph (i.e., a reference graph that represents all loci in a substantial portion of the genome). Thus storing graph elements (e.g., nodes and edges) using a library of objects with native pointers or other implementation that provides index-free adjacency actually improves the ability of the technology to provide storage, retrieval, and alignment for genomic information since it uses the physical memory of a computer in a particular way.

While no specific format is required for storage of a graph, FIGS. 8 and 9 are presented to illustrate useful formats. In some embodiments, methods of the invention use the stored graph with sequence reads that are obtained from a subject. In some embodiments, sequence reads are obtained as an electronic article, e.g., uploaded, emailed, or FTP transferred from a lab to system 701. In certain embodiments, sequence reads are obtained by sequencing.

Figure 10:
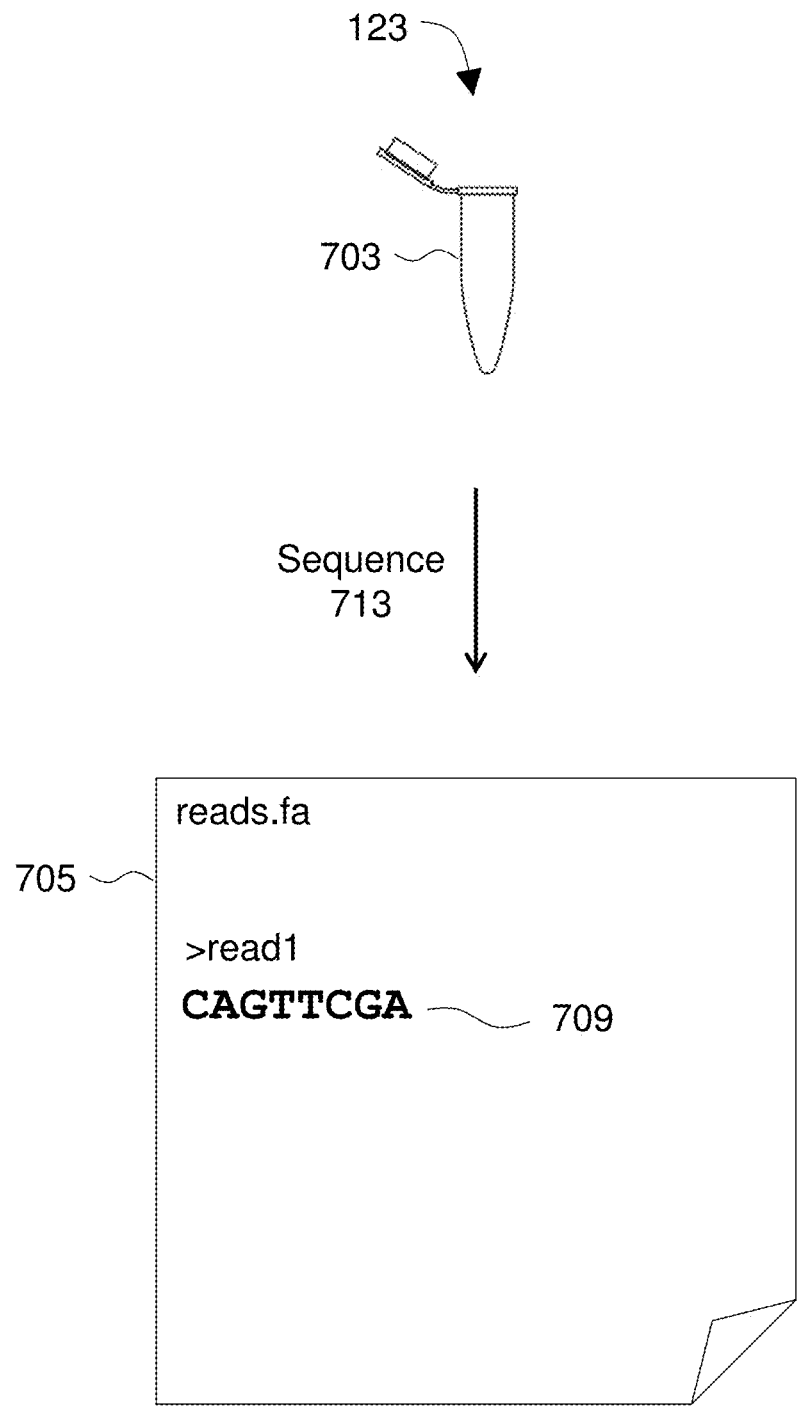
FIG. 10 illustrates a method of generating sequence reads from a sample.

FIG. 10 illustrates obtaining 123 a set of sequence reads 705 from a sample 703. As a preliminary step (not depicted), nucleic acid may be isolated and/or enriched.

In certain embodiments, sequence reads are obtained by performing sequencing 713 on a sample 703 from a subject (however in some embodiments, sequence reads are obtained when a read file is transferred into a system of the invention). Sequencing may be by any method and sequencing instrument known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems and sequencing instruments sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024; 5,674,713; and U.S. Pat. No. 5,700,673, each incorporated by reference. 454 sequencing involves two steps. First, DNA is sheared into blunt-end fragments attached to capture beads and then amplified in droplets. Second, pyrosequencing is performed on each DNA fragment in parallel. Addition of nucleotides generates a light signal that is recorded by a CCD camera in a sequencing instrument.

Another sequencing technique and instrument that can be used is SOLiD technology by Applied Biosystems from Life Technologies Corporation (Carlsbad, Calif.). In SOLiD sequencing, genomic DNA is sheared into fragments, and adaptors are attached to generate a fragment library. Clonal bead populations are prepared in microreactors containing beads, primers, template, and PCR components. Following PCR, the templates are denatured and enriched and the sequence is determined by a process that includes sequential hybridization and ligation of fluorescently labeled oligonucleotides.

Another example of a DNA sequencing technique and instrument that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. Addition of one or more nucleotides releases a proton (H+), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

As shown in FIG. 10, sequencing 713 generates a set of sequence reads 705. Reads according to the invention generally include sequences of nucleotide data anywhere from tens to thousands of bases in length. A set of sequence reads 705 will typically be provided in a suitable format such as, for example, a FASTA or FASTQ file. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 123 in a format such as FASTA, FASTQ, or similar.

In some embodiments, the sequence reads 705 are assembled to provide a contig or consensus sequence, which contig or consensus sequence may be used in finding alignments to a reference graph. Sequence assembly may include any suitable methods known in the art including de novo assembly, reference-guided assembly, others, or combinations thereof. In a preferred embodiment, sequence reads are assembled using graph-based alignment methods. See, e.g., U.S. Pub. 2015/0057946 and U.S. Pub. 2015/0056613, both incorporated by reference. Embodiments of a graph and its use are discussed in greater detail below. The result of assembly is a sequence representing the corresponding portion of the original nucleic acid. The contig or consensus sequence or one or more of individual sequence read 709 may be mapped to a reference graph to find an alignment with an optimal score.

In certain embodiments, each sequence read 709 is mapped to a reference graph and an alignment is found. As previously noted, alignments of sequence reads to a reference graph may be used as evidence to identify the likelihood of the possible diploid genotypes from an interval in a reference graph.

Figure 11:
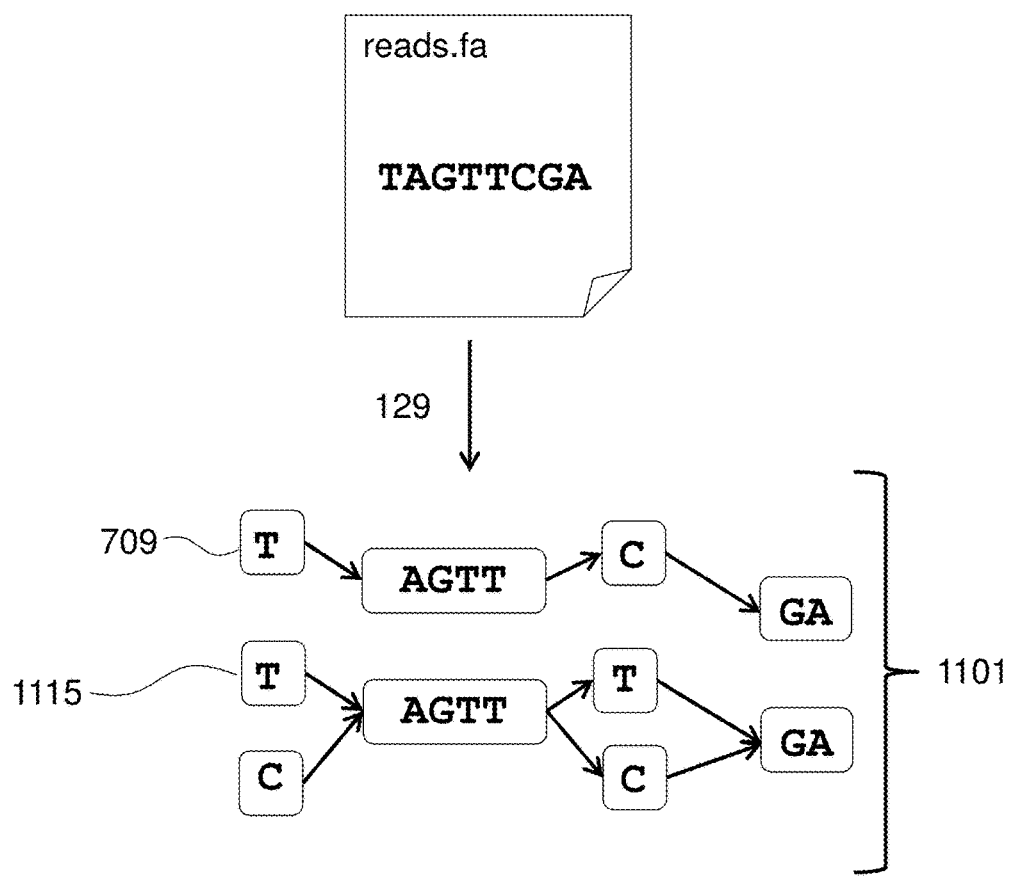
FIG. 11 illustrates finding alignments between a sequence and a reference graph.

FIG. 11 illustrates finding alignments 1101 between a sequence read 709 and a reference graph 1115. Using alignment operations of the invention, reads 709 can be rapidly mapped to the reference graph 1115 despite their large numbers or short lengths. Numerous benefits obtain by using a graph as a reference. For example, aligning against a graph is more accurate than aligning against a linear reference and then attempting to adjust one's results in light of other extrinsic information. This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions). A modified Smith-Waterman operation for comparing a sequence to a reference graph is provided here as an extension of pairwise alignment methods.

Pairwise alignment generally involves placing one sequence along part of a target, introducing gaps according to an algorithm, scoring how well the two sequences match, and preferably repeating for various positions along the reference. The best-scoring match is deemed to be the alignment and represents an inference of homology between aligned portions of the sequences. In some embodiments, scoring an alignment of a pair of nucleic acid sequences involves setting values for the probabilities of substitutions and indels. When individual bases are aligned, a match or mismatch contributes to the alignment score by a substitution score, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affects the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i) $|x'|=|y'|$; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]); (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

Any pair may have a score a defined by a 4×4 matrix B of substitution probabilities. For example, B(i,i)=1 and 0<B(i,j)<1 [for i≠j], is one possible scoring system. For instance, where a transition is thought to be more biologically probable than a transversion, matrix B could include B(C,T)=0.7 and B(A,T)=0.3, or other values desired or determined by methods known in the art.

A pairwise alignment, generally, involves—for sequence Q (query) having m characters and a reference genome T (target) of n characters—finding and evaluating possible local alignments between Q and T. For any $1 \leq i \leq n$ and $1 \leq j \leq m$, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from $O(m^2n)$ to $O(mn)$ where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The original Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The original SW algorithm is expressed for an n×m matrix H, representing the two strings of length n and m, in terms of equation (1):

$$H\_k0 = H\_0l = 0 \text{(for } 0 \le k \le n \text{ and } 0 \le l \le m)$$

$$H\_ij = \max\{H\_(i-1,j-1) + s(a\_i, b\_j), H\_(i-1,j) - W\_in, H\_(i,j-1) - W\_del, 0\}$$

$$(\text{for } 1 \le i \le n \text{ and } 1 \le j \le m) \quad (1)$$

In the equations above, s(ai,bj) represents either a match bonus (when ai=bj) or a mismatch penalty (when ai≠bj), and insertions and deletions are given the penalties Win and Wdel, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi-1,j-1, Hi-1,j, or Hi,j-1) was used to compute the final maximum value for each cell. The backtracking stops when a zero is reached. The optimal-scoring alignment may contain greater than the minimum possible number of insertions and deletions, while containing far fewer than the maximum possible number of substitutions.

SW or SW-Gotoh may be implemented using dynamic programming to perform local sequence alignment of the two strings, S and A, of sizes m and n, respectively. This dynamic programming employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) \text{ (for } 0 < j < m, 0 < k < n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j,k] = \max(p[j-1,k-1], i[j-1,k-1], d[j-1,k-1]) + \text{MISMATCH\_PEN, if } S[j] \ne A[k]$$

$$= \max(p[j-1,k-1], i[j-1,k-1], d[j-1,k-1]) + \text{MATCH\_BONUS, if } S[j] = A[k] \quad (3)$$

the insertion argument i[j,k], is given by equation (4), below:

$$i[j,k] = \max(p[j-1,k] + \text{OPENING\_PEN}, i[j-1,k], d[j-1,k] + \text{OPENING\_PEN}) + \text{INSERTION\_PEN} \quad (4)$$

and the deletion argument d[j,k], is given by equation (5), below:

$$d[j,k] = \max(p[j,k-1] + \text{OPENING\_PEN}, i[j,k-1] + \text{OPENING\_PEN}, d[j,k-1]) + \text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:

MATCH_BONUS: 10
MISMATCH_PEN: −20
INSERTION_PEN: −40
OPENING_PEN: −10
DELETION_PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention use a modified Smith-Waterman operation that involves a multi-dimensional look-back through a reference graph. Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the graph-type reference. That alignment algorithm identifies the maximum value for Ci,j by identifying the maximum score with respect to each sequence contained at a position on the graph. In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic graph system that employs physical memory addressing (e.g., through the use of native pointers or index free adjacency as discussed above). The combination of multi-dimensional alignment to a reference graph with the use of spatial memory addresses (e.g., native pointers or index-free adjacency) improves what the computer system is capable of, facilitating whole genomic scale analysis to be performed using the methods described herein.

The operation includes aligning a sequence, or string, to a graph. For the purpose of defining the algorithm, let S be the string being aligned, and let D be the directed graph to which S is being aligned. The elements of the string, S, are bracketed with indices beginning at 1. Thus, if S is the string ATCGAA, S[1]=A, S[4]=G, etc.

In certain embodiments, for the graph, each letter of the sequence of a node will be represented as a separate element, d. In a preferred embodiment, node or edge objects contain the sequences and the sequences are stored as the longest-possible string in each object. A predecessor of d is defined as:

(i) If d is not the first letter of the sequence of its object, the letter preceding d in its object is its (only) predecessor;

(ii) If d is the first letter of the sequence of its object, the last letter of the sequence of any object that is a parent of d's object is a predecessor of d.

The set of all predecessors is, in turn, represented as P[d].

In order to find the "best" alignment, the algorithm seeks the value of M[j,d], the score of the optimal alignment of the first j elements of S with the portion of the graph preceding (and including) d. This step is similar to finding Hi,j in equation 1 above. Specifically, determining M[j,d] involves finding the maximum of a, i, e, and 0, as defined below:

$$M[j,d]=\max\{a,i,e,0\} \qquad (6)$$

where
e=max{M[j, p*]+DELETE_PEN} for p* in P[d]
i=M[j−1, d]+INSERT_PEN
a=max{M[j−1, p*]+MATCH_SCORE} for p* in P[d], if S[j]=d;
    max{M[j−1, p*]+MISMATCH_PEN} for p* in P[d], if S[j]≠d As described above, e is the highest of the alignments of the first j characters of S with the portions of the graph up to, but not including, d, plus an additional DELETE_PEN. Accordingly, if d is not the first letter of the sequence of the object, then there is only one predecessor, p, and the alignment score of the first j characters of S with the graph (up-to-and-including p) is equivalent to M[j,p]+DELETE_PEN. In the instance where d is the first letter of the sequence of its object, there can be multiple possible predecessors, and because the DELETE_PEN is constant, maximizing [M[j, p*]+DELETE_PEN] is the same as choosing the predecessor with the highest alignment score with the first j characters of S.

In equation (6), i is the alignment of the first j−1 characters of the string S with the graph up-to-and-including d, plus an INSERT_PEN, which is similar to the definition of the insertion argument in SW (see equation 1).

Additionally, a is the highest of the alignments of the first j characters of S with the portions of the graph up to, but not including d, plus either a MATCH_SCORE (if the jth character of S is the same as the character d) or a MISMATCH_PEN (if the jth character of S is not the same as the character d). As with e, this means that if d is not the first letter of the sequence of its object, then there is only one predecessor, i.e., p. That means a is the alignment score of the first j−1 characters of S with the graph (up-to-and-including p), i.e., M[j−1,p], with either a MISMATCH_PEN or MATCH_SCORE added, depending upon whether d and the jth character of S match. In the instance where d is the first letter of the sequence of its object, there can be multiple possible predecessors. In this case, maximizing {M[j, p*]+ MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for a sequence reads 709 to the reference graph 1715 by calculating not only the insertion, deletion, and match scores for that element, but looking backward (against the direction of the graph) to any prior nodes on the graph to find a maximum score.

Figure 12:
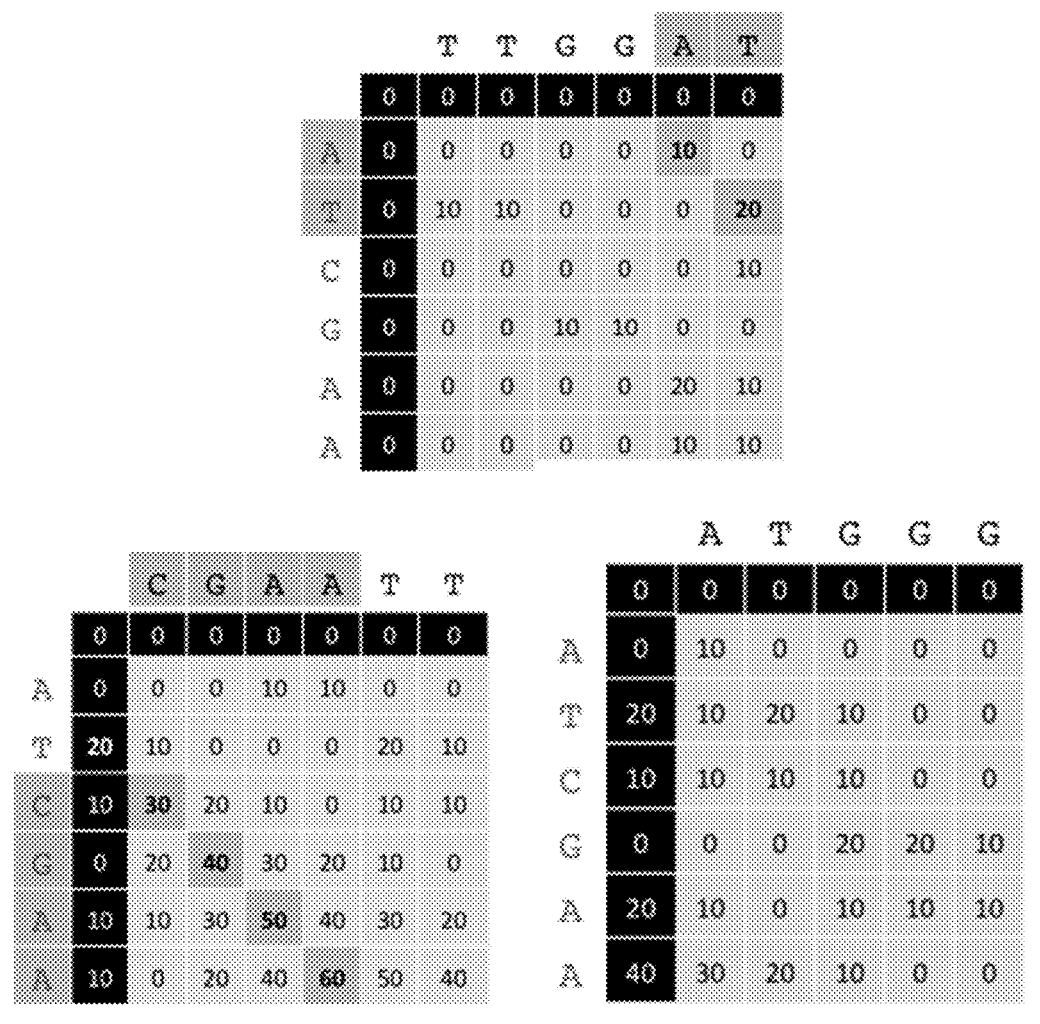

FIG. 12 shows the matrices that represent the comparison. The modified Smith-Waterman operation of the invention identifies the highest score and performs a backtrack to identify the proper alignment of the sequence. See, e.g., U.S. Pub. 2015/0057946 and U.S. Pub. 2015/0056613, both incorporated by reference. Systems and methods of the invention can be used to provide a report that identifies a modified base at the position within the genome of the subject. Other information may be found in Kehr et al., 2014, Genome alignment with graph data structures: a comparison, BMC Bioinformatics 15:99 and Lee, 2003, Generating consensus sequences from partial order multiple sequence alignment graphs, Bioinformatics 19(8):999-1008, both incorporated by reference. Thus, analyzing genomic information from nucleic acid from the sample 703 may include aligning one or more of the sequence reads 709 to the reference graph 1715 as shown in FIG. 11. The branches to which the reads 709 have been aligned are identified, along with the corresponding species.

Figure 13:
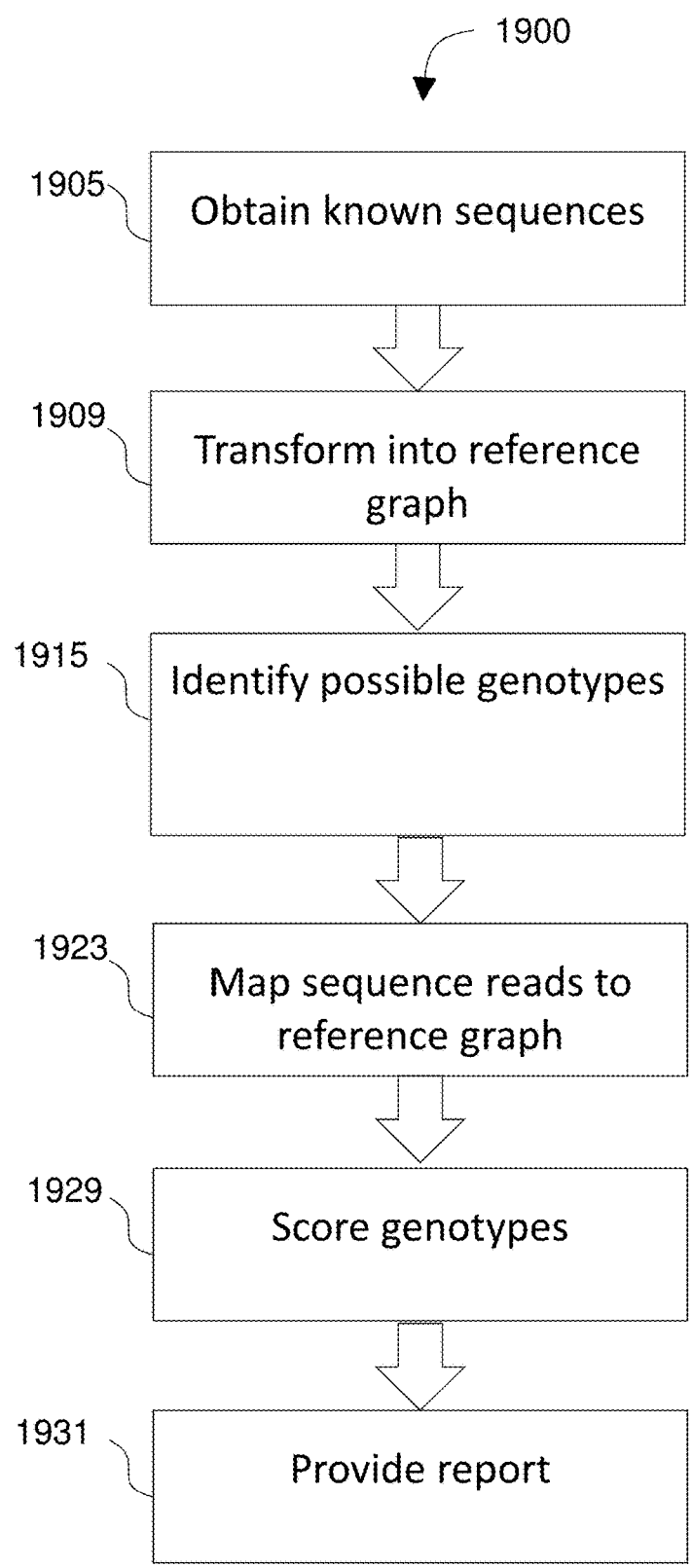
FIG. 13 diagrams a method for determining a genotype of a subject.

FIG. 13 diagrams a method 1900 for determining a genotype of a subject. The method 1900 includes obtaining 1905 known sequences and transforming 1909 the known sequences into a reference graph. The known sequences are that set of available sequences that are used as reference material for analyzing the subject being studied. For example, all or a sampling of all available human genomes spanning the relevant portion (e.g., gene, operon, chromosome, or complete genome). The reference graph includes nodes connected by edges into a plurality of paths, the plurality of paths including a first path representing a first haplotype A and a second path representing a second haplotype B. The method 1900 includes identifying 1915 at least a first genotype AA, a second genotype AB, and a third genotype BB corresponding to the first haplotype A and the second haplotype B. Sequence reads are obtained and mapped 1923 to the reference graph. Sequence reads may be obtained by sequencing nucleic acid from a sample from a subject. The method 1900 includes assigning scores 1929 to each of the first genotype AA, the second genotype AB, and the third genotype BB, wherein the scores correspond to a result of mapping sequence reads from an organism to the reference graph and identifying for the organism a one of the first genotype AA, the second genotype AB, and the third genotype BB having a highest assigned score. Subsequent genotypes may be similarly scored, and the full genotype may then be determined using dynamic programming. A report is provided 1931 with the genotype of the organism.

The plurality of known sequences are stored as a reference graph comprising objects in the tangible memory subsystem, wherein matching homologous segments of the known sequences are each represented by a single object in the reference graph. Objects of the reference graph may include vertex objects connected by edge objects and an adjacency list for each vertex object and edge object, wherein the adjacency list for a vertex object or edge object lists the edge objects or vertex objects to which that vertex object or edge object is adjacent. Each entry in an adjacency list may be a pointer to the adjacent vertex object or edge object, wherein each pointer identifies a physical location in the memory subsystem at which the adjacent object is stored. In some embodiments, the reference graph uses index-free adjacency to link the objects into paths to represent the known sequences from the plurality of different species. Further discussion may be found in U.S. Pub. 2013/0073214; U.S. Pub. 2013/0345066; U.S. Pub. 2013/

0311106; U.S. Pub. 2013/0059740; U.S. Pub. 2012/0157322; U.S. Pub. 2015/0057946 and U.S. Pub. 2015/0056613, each incorporated by reference for all purposes.

The method 101 further includes obtaining 123 a genetic sequence from an organism and finding alignments 127 between the genetic sequence and the plurality of known sequences from the plurality of different species. A report is provided that includes a description of a genotype of the organism based on a result of the aligning step.

Figure 14:
FIG. 14 illustrates a report that may be generated.

FIG. 14 illustrates a report 2035 that may be generated by the system 701. The report 2035 was generated in this illustrated example by following the bottom-most path through the traversal graph 501 shown in FIG. 5. Thus the report 2035 includes a description of the determined genotypes (i.e., the full genotype) for some hypothetical organism.

Thus, genomic references are structured as a reference graph that represents genetic variation in organisms. A path through a series of connected nodes and edges represents a genetic sequence. Genetic variation within a diploid organism is represented by multiple paths through the reference graph. The graph may be transformed into a traversal graph in which a path represents a diploid genotype. Genetic analysis using the traversal graph allows an organism's diploid genotype to be elucidated, e.g., by mapping sequence reads to the reference graph and scoring paths in the traversal graph based on the mapping to determine the path through the traversal graph that best fits the sequence reads.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of determining a genotype, the method comprising:
providing a reference graph in computer memory, the reference graph representing a plurality of genomic sequences and comprising nodes connected by edges into a plurality of paths, wherein variation across the plurality of genomic sequences is incorporated as divergent paths converging to nodes representing conserved sequence, such that each of the plurality of genomic sequences is represented as a path in the reference graph;
wherein the plurality of paths further comprises a first alternate path representing a first haplotype A at a position and a second alternate path representing a second haplotype B at the position, wherein each of the first and second alternate paths converge to a node representing a conserved sequence;
identifying one or more genotypes corresponding to either or both of the first haplotype A and the second haplotype B, the one or more genotypes comprising a first genotype AA, a second genotype AB, and a third genotype BB;
mapping a plurality of sequence reads from an organism to the reference graph, wherein the mapping comprises looking backwards to predecessor paths to identify an optimal location for a sequence read across multiple alternate paths;
assigning, based on properties of the mapped plurality of sequence reads to the reference graph, scores to each of the identified genotypes, wherein the assigning considers whether a sequence read mapping to the first haplotype A changes the probability of the genotype including the second haplotype B; and
identifying one of the first genotype AA, second genotype AB, or third genotype BB as having a highest score in said assigning step, thereby providing a genotype.

2. The method of claim 1, wherein the properties of the mapped reads are selected from the group consisting of position, count, and quality.

3. The method of claim 1, further comprising enumerating a plurality of genotypes based on a plurality of haplotypes in the reference graph, assigning scores to each genotype, and identifying a most likely sequence of genotypes for the organism using dynamic programming.

4. The method of claim 3, wherein the dynamic programming comprises using Viterbi decoding.

5. The method of claim 1, wherein the plurality of sequence reads represent at least a majority of a genome of an organism.

6. The method of claim 1, further comprising:
representing the first genotype AA, the second genotype AB, and the third genotype BB using a traversal graph comprising nodes connected by edges into a plurality of paths, the plurality of paths including a first traversal path representing the first genotype AA, a second traversal path representing the second genotype AB, and a third traversal path representing the third genotype BB; and
determining weights for the first traversal path, the second traversal path, and the third traversal path based on properties of the sequence reads that map to the reference graph.

7. The method of claim 6, further comprising enumerating a plurality of genotypes from the reference graph, representing the plurality of genotypes as paths in the traversal graph, and identifying the most likely sequence of genotypes by determining a most probable path through the traversal graph.

8. The method of claim 7, wherein identifying the most likely sequence of genotypes by determining a most probable path through the traversal graph comprises using dynamic programming.

9. The method of claim 8, wherein using dynamic programming comprises using a Dijkstra operation to find a least-cost path.

10. The method of claim 1, wherein A represents an allele of a gene known to be dominant and B represents an allele of the gene known to be recessive.

11. The method of claim 10, wherein the organism is a patient, the method further comprising providing a report for the patient that reports the identified one of the first genotype AA, the second genotype AB, and the third genotype BB.

12. The method of claim 1, wherein providing a reference graph further comprises obtaining the plurality of genomic sequences and transforming the plurality of genomic sequences into a reference graph, wherein matching homologous segments of the known sequences are each represented by a single object in the reference graph.

13. The method of claim 12, wherein matching homologous segments of the plurality of genomic sequences are each represented by a single node.

14. The method of claim 12, wherein assigning scores to each of the identified genotypes comprises determining the likelihood of sequence reads mapping to each edge of a reference graph given each possible state.

15. A system for determining a genotype, the system comprising a processor coupled to a tangible memory subsystem having stored therein:
a reference graph representing a plurality of genomic sequences and comprising nodes connected by edges into a plurality of paths, wherein variation across the plurality of genomic sequences is incorporated as divergent paths converging to nodes representing conserved sequence, such that each of the plurality of genomic sequences is represented as a path in the reference graph;
wherein the plurality of paths further comprises a first alternate path representing a first haplotype A at a position and a second alternate path representing a second haplotype B at the position, wherein each of the first and second alternate paths converge to a node representing a conserved sequence; and
instructions that when executed by the processor cause the system to:
identify one or more genotypes corresponding to either or both of the first haplotype A and the second haplotype B, the one or more genotypes comprising a first genotype AA, a second genotype AB, and a third genotype BB;
map a plurality of sequence reads from an organism to the reference graph, wherein the mapping comprises looking backwards to predecessor paths to identify an optimal location for a sequence read across multiple alternate paths;
assign—based on properties of the mapped plurality of sequence reads to the reference graph—scores to each of the identified genotypes, wherein the assigning considers whether a sequence read mapping to the first haplotype A changes the probability of the genotype including the second haplotype B; and
identify one of the first genotype AA, second genotype AB, or third genotype BB as having a highest score in said assigning step, thereby providing a genotype.

16. The system of claim 15, wherein the instructions are further operable to:
represent the first genotype AA, the second genotype AB, and the third genotype BB using a traversal graph comprising nodes connected by edges into a plurality of paths, the plurality of paths including a first traversal path representing the first genotype AA, a second traversal path representing the second genotype AB, and a third traversal path representing the third genotype BB; and
determine weights for the first traversal path, the second traversal path, and the third traversal path based on numbers of the sequence reads that map to the traversal graph.

17. The system of claim 16, wherein the instructions are further operable to:
enumerate a plurality of genotypes from the reference graph;
represent the plurality of genotypes as paths in the traversal graph; and
identify the most likely sequence of genotypes by determining a most probable path through the traversal graph.

18. The system of claim 17, wherein identifying the most likely sequence of genotypes by determining a most probable path through the traversal graph comprises using dynamic programming.

19. The system of claim 18, wherein using dynamic programming comprises using a Dijkstra operation to find a least-cost path.

20. The system of claim 15, wherein the organism is a patient and the system is operable to provide a report for the patient that gives the identified one of the first genotype AA, the second genotype AB, and the third genotype BB.

* * * * *